(12) United States Patent
Parker et al.

(10) Patent No.: US 12,318,418 B2
(45) Date of Patent: Jun. 3, 2025

(54) MODIFIED ADENOVIRUSES

(71) Applicant: UNIVERSITY COLLEGE CARDIFF CONSULTANTS LTD, South Glamorgan (GB)

(72) Inventors: Alan Parker, South Glamorgan (GB); Hanni Uusi-Kerttula, Helsinki (FI)

(73) Assignee: UNIVERSITY COLLEGE CARDIFF CONSULTANTS LIMITED, Wales (GB)

( * ) Notice: Subject to any disclaimer, the term of this patent is extended or adjusted under 35 U.S.C. 154(b) by 1084 days.

(21) Appl. No.: 16/970,003

(22) PCT Filed: Feb. 13, 2019

(86) PCT No.: PCT/GB2019/050380
§ 371 (c)(1),
(2) Date: Aug. 14, 2020

(87) PCT Pub. No.: WO2019/158914
PCT Pub. Date: Aug. 22, 2019

(65) Prior Publication Data
US 2021/0100855 A1    Apr. 8, 2021

(30) Foreign Application Priority Data
Feb. 16, 2018   (GB) ...................... 1802539

(51) Int. Cl.
*A61K 35/761* (2015.01)
*A61P 35/00* (2006.01)
*C12N 7/00* (2006.01)

(52) U.S. Cl.
CPC ............ *A61K 35/761* (2013.01); *A61P 35/00* (2018.01); *C12N 7/00* (2013.01)

(58) Field of Classification Search
CPC ......... A61K 35/761; A61P 35/00; C12N 7/00; C12N 2710/10321; C12N 2710/10322; C12N 2710/10332; C12N 2710/10345
See application file for complete search history.

(56) References Cited

U.S. PATENT DOCUMENTS 8,974,777 B2 *   3/2015   Cascallo Piqueras .. A61P 35/00
                                                    435/320.1

FOREIGN PATENT DOCUMENTS

WO       03062400 A      7/2003
WO    2004099422 A      11/2004
(Continued)

OTHER PUBLICATIONS

Uusi-Kerttula et al., Incorporation of Peptides Targeting EGFR and FGFR1 into the Adenoviral Fiber Knob Domain and Their Evaluation as Targeted Cancer Therapies, Human Gene Therapy, 26: 320-329. (Year: 2015).*

(Continued)

*Primary Examiner* — Ram R Shukla
*Assistant Examiner* — Shabana S Meyering
(74) *Attorney, Agent, or Firm* — Duane Morris LLP; Thomas J. Kowalski

(57) ABSTRACT

The invention concerns a modified oncolytic adenovirus of serotype Ad5; a pharmaceutical composition comprising same; and a method of treating cancer using same wherein said modified adenovirus comprises at least one point mutation(s) in the hexon hypervariable region 7 (HVR7 mutation) to prevent virus binding with coagulation factor 10 (FX); at least one point mutation(s) in the fiber knob region AB loop (KO1 mutation) to prevent virus binding with the coxsackie and adenovirus receptor (CAR); and at least one (Continued)

Figure 2A:
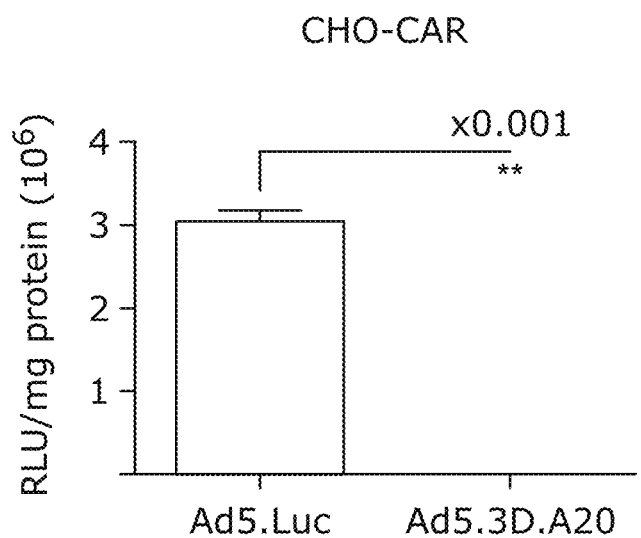

point mutation(s) in the penton integrin binding motif Arg-Gly-Asp (RGD) to prevent virus binding with $\alpha_v\beta_3/\alpha_v\beta_5$ integrin.

26 Claims, 29 Drawing Sheets

Specification includes a Sequence Listing.

(56) References Cited

FOREIGN PATENT DOCUMENTS

| | | | | |
|---|---|---|---|---|
| WO | WO-2007039728 A2 * | 4/2007 | ............. | A61K 49/00 |
| WO | WO-2009098492 A2 * | 8/2009 | ............. | A61K 35/58 |
| WO | 2016118433 A | 7/2016 | | |
| WO | WO-2016118433 A1 * | 7/2016 | ............. | A61K 35/76 |

OTHER PUBLICATIONS

Wang et al., Mutation in fiber of adenovirus serotype 5 gene therapy vector decreases liver tropism, International Journal of Clinical and Experimental Medicine, 7(12):4942-4950. (Year: 2014).*
Bai et al., Mutations That Alter an Arg-Gly-Asp (RGD) Sequence in the Adenovirus Type 2 Penton Base Protein Abolish Its Cell-Rounding Activity and Delay Virus Reproduction in Flat Cells, Journal of Virology, 67(9): 5198-5205. (Year: 1993).*
Uusi-Kerttula et al., (26:320-329, Human Gene Therapy, 2015) (Year: 2015).*
Mizuguchi et al., (A simplified system for constructing recombinant adenoviral vectors containing heterologous peptides in the HI loop of their fiber knob. Gene Ther 8, 730-735 (2001) (Year: 2001).*
Morgan et al., J. Biophys Biochem Cytol. May 24, 1957; 3(3):505-8 (Year: 1957).*
Flickinger et al., J. Immunother Cancer, 2020; 8:e001046 (Year: 2020).*
Alba et al., Blood Jul. 30, 2009; 114(5):965-971 (Year: 2009).*
Smith et al., Molecular Therapy vol. 5, No. 6, Jun. 2002 pp. 770-779 (Year: 2002).*
Di Paolo et al., Immunity, Jul. 17, 2009; 31(1): 110-121 (Year: 2009).*
Kirby et al., Journal of Virology, Mar. 2000, pp. 2804-2813 (Year: 2000).*
Kreppel et al., Molecular Therapy vol. 12, No. 1, Jul. 2005 (Year: 2005).*
Mato-Berciano et al., Journal of Controlled Release 332 (2021), pp. 517-528 (Year: 2021).*
Rojas et al., Journal of Controlled Release 237 (2016), pp. 78-88 (Year: 2016).*
Vigant et al., Molecular Therapy vol. 16, No. 8, Aug. 2008 (Year: 2008).*
Waddington et al., Cell 132, pp. 397-409, Feb. 8, 2008 (Year: 2008).*
ATCC® Catalog No. VR-1516, https://www.atcc.org/~/media/0df7351153724bd6a3e7d78d5ba2f933, retrived Apr. 29, 2024 (Year: 2024).*
Adenovirus 5 availability from Applied Biological Materials Inc., Richmond, BC, Canada, printed from abmgood.com/adenovirus-5-adenovirus.html (Year: 2021).*
Adenovirus 5 availability from The Native Antigen Company, Oxfordshire, United Kingdom, printed from thenati veantigencom pany. com/products/ adenovirus-type-5-parti cl es-wild-type-copy (Year: 2021).*
Bai et al., vol. 67, No. 9, p. 5198-5205, Journal of Virology, 1993) (Year: 1993).*
Coughlan L. et al., Viruses, 2(10), 2290-2355, 2010 (Year: 2010).*
COBALT_alignment of Penton Sequences from Ad5 and Ad2 (Year: 2008).*
COBALT_alignment of Hexon Sequences from Ad5 (Year: 2008).*
Parker, Alan L., et al., Multiple vitamin K-dependent coagulation zymogens promote adenovirus-mediated gene delivery to hepatocytes, Blood, American Society of Hematology, vol. 108, No. 8, Oct. 1, 2006 (online Jun. 20, 2006).
Parker, Alan L., et al., Influence of Coagulation Factor Zymogens on the Infectivity of Adenoviruses Pseudotyped with Fibers from Subgroup D, Journal of Virology, vol. 81, No. 7, Apr. 1, 2007, p. 3627-3631.
Kurachi, S., et al., Characterization of capsid-modified adenovirus vectors containing heterologous peptides In the fiber knob, protein IX, or hexon, Gene Therapy (2007) vol. 14, No. 3 p. 266-274.
Uusi-Kerttula, Hanni, et al., Pseudotyped avb6 integrin-targeted adenovirus ventors for ovarian cancer therapies, Oncotarget, vol. 7, No. 19, p. 27926-27937.
Waddington, Simon N., et al., Adenovirus Serotype 5 Hexon Mediates Liver Gene Transfer, Cell 132, 397-409, Feb. 8, 2008, Elsevier Inc.
Bradshaw, Angela C., et al., Requirements for Receptor Engagement during Infection by Adenovirus Complexed with Blood Coagulation Factor X, PLoS Pathogens, vol. 6, Oct. 2010.
Coughlan, Lynda, et al., Tropism-Modification Strategies for Targeted Gene Delivery Using Adenoviral Vectors, Viruses 2010, 2, 2290-2355.
UK IPO Search Report for GB1802539.5 dated Oct. 19, 2018.
International Search Report and Written Opinion in PCT/GB2019/050380, dated Apr. 17, 2019.
R Alemany and DT Curiel, Brief Communication: CAR-binding ablation does not change biodistribution and toxicity of adenoviral vectors, Gene Therapy (2001) 8, 1347-1353.
Lynda Coughlan, et al., Ad5:Ad48 Hexon Hypervariable Region Substitutions Lead to Toxicity and Increased Inflammatory Responses Following Intravenous Delivery, Molecular Therapy (2012) vol. 20 No. 12, 2268-2281.
Campbell G. Nicol, et al., Effect of Adenovirus Serotype 5 Fiber and Penton Modifications on in Vivo Tropism in Rats, Molecular Therapy (Aug. 2004) vol. 10, No. 2, 344-354.
Alan L. Parker, et al., Multiple vitamin K-dependent coagulation zymogens promote adenovirus-mediated gene delivery to hepatocytes, Blood, (Oct. 15, 2006) vol. 108, No. 8, 2554-2561.
Theodore Smith, et al., In Vivo Hepatic Adenoviral Gene Delivery Occurs Independently of the Coxsackievirus—Adenovirus Receptor, Molecular Therapy (Jun. 2002) vol. 5, No. 6, 771-779.
Uusi-Kerttula et al., "A tropism-modified αvβ6 integrin-selective adenoviral vector for epithelial ovarian cancer therapies", British Society for Gene and Cell Therapy Annual Conference and Joint UK Regenerative Medicine Platform Meeting, Royal Welsh College of Music & Drama, Cardiff, Wales, United Kingdom, BSGCT Special Lecture & Fairbairn Award Presentations), Concert Hall, Apr. 19, 2017 (Abstract published in Human Gene Therapy vol. 28(8), Aug. 1, 2017, and available at https://doi.org/10.1089/hum.2017.29044.abstracts).
Simon N. Waddington, et al., Adenovirus Serotype 5 Hexon Mediates Liver Gene Transfer, Cell (Feb. 8, 2008) 132, 397-409.

* cited by examiner

| Vector | Titre (vp/ml) | | Receptor binding | | | |
|---|---|---|---|---|---|---|
| | Repl. def. | Oncolytic | αvβ3/5 | αvβ6 | CAR | FX |
| Ad5.Luc | 3.9 x 10$^{12}$ | 1.1 x 10$^{12}$ | + | – | + | + |
| Ad5.KO1.HVR7.RGE.A20 'Ad5.3D.A20' | 3.0 x 10$^{12}$ | 1.5 x 10$^{12}$ | – | + | – | – |
FIG. 1A
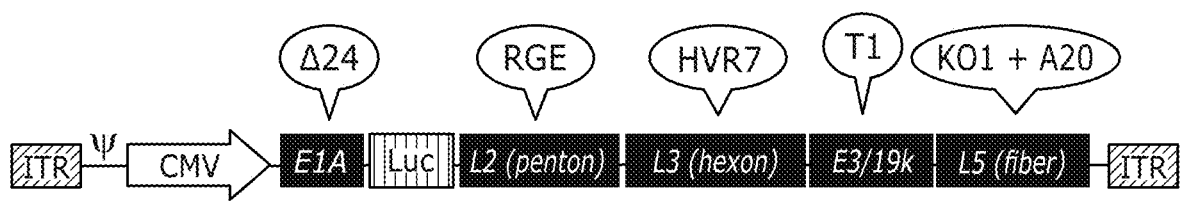
FIG. 1B
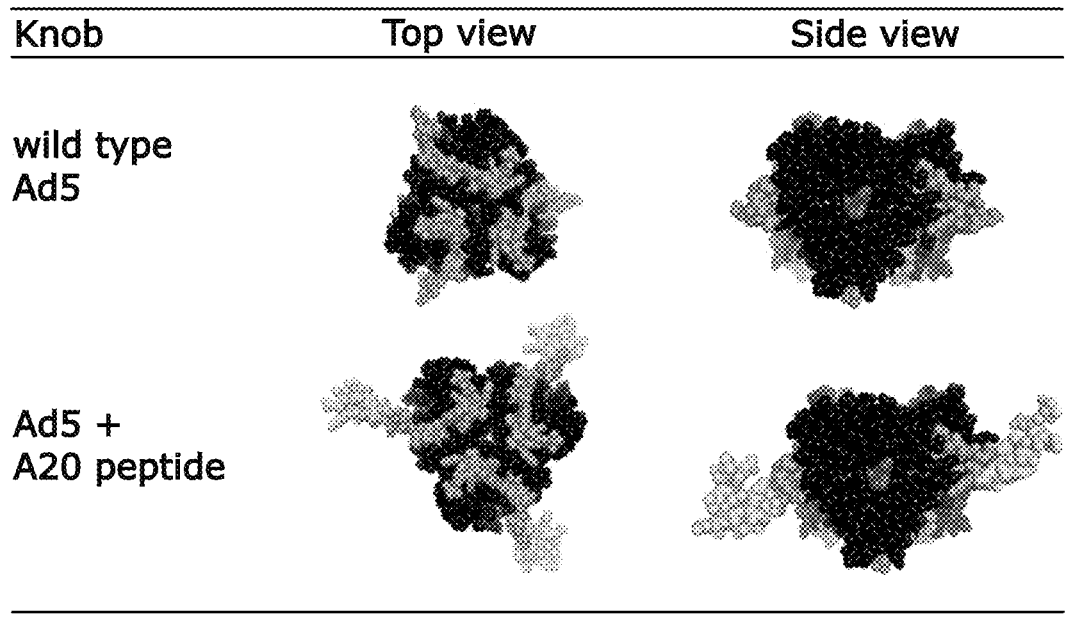
FIG. 1C ○ PBS
▲ Ad5.Luc
★ Ad5.3D.A20

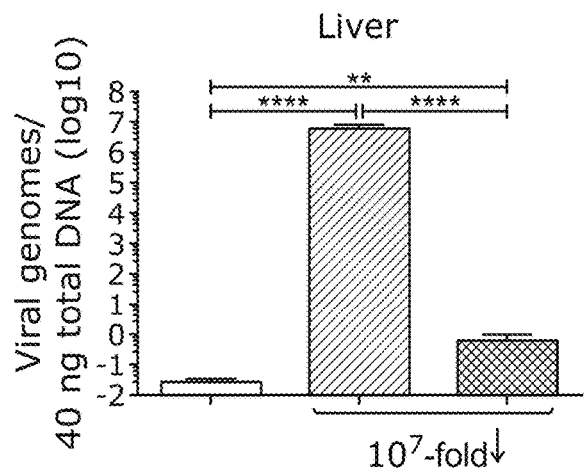
FIG. 6A
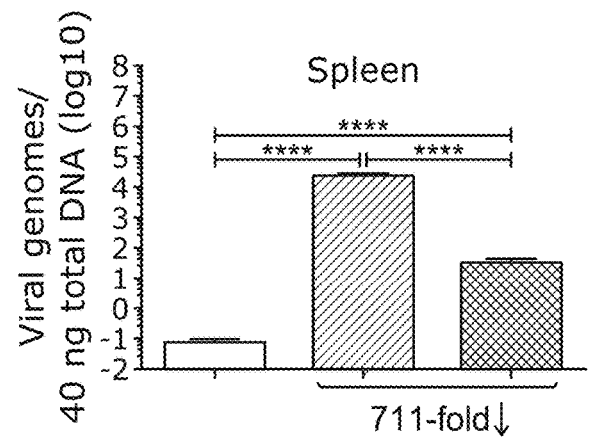
FIG. 6B
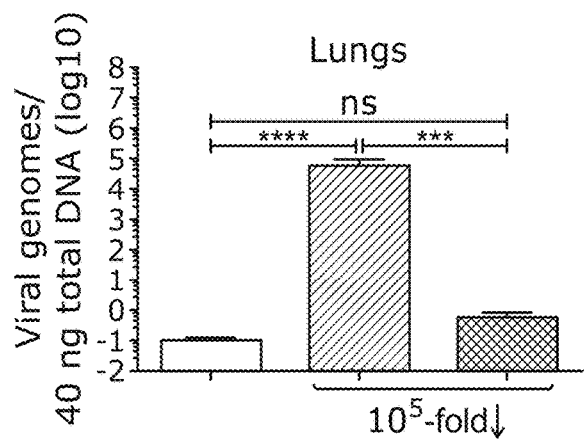
FIG. 6C
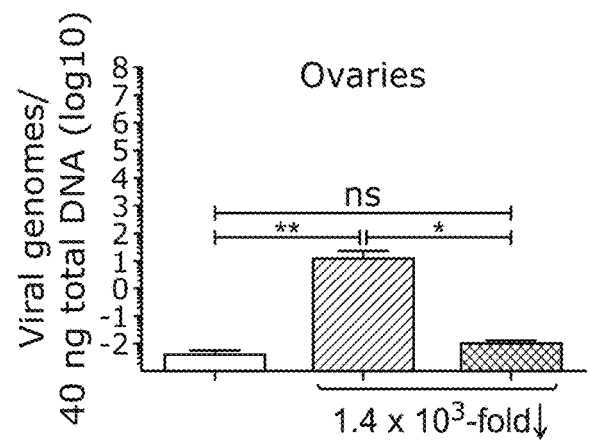
FIG. 6D
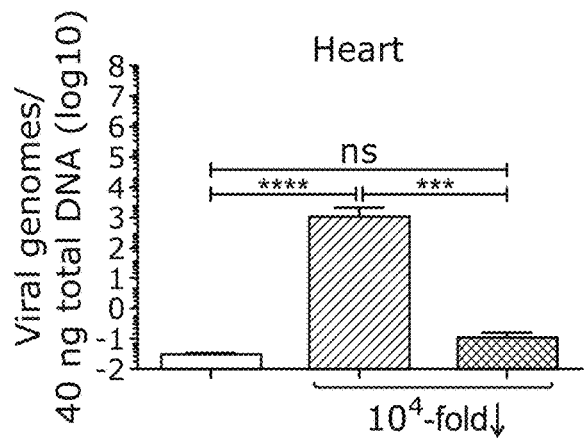
FIG. 6E
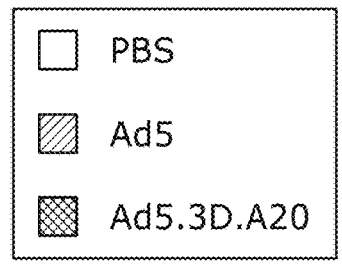

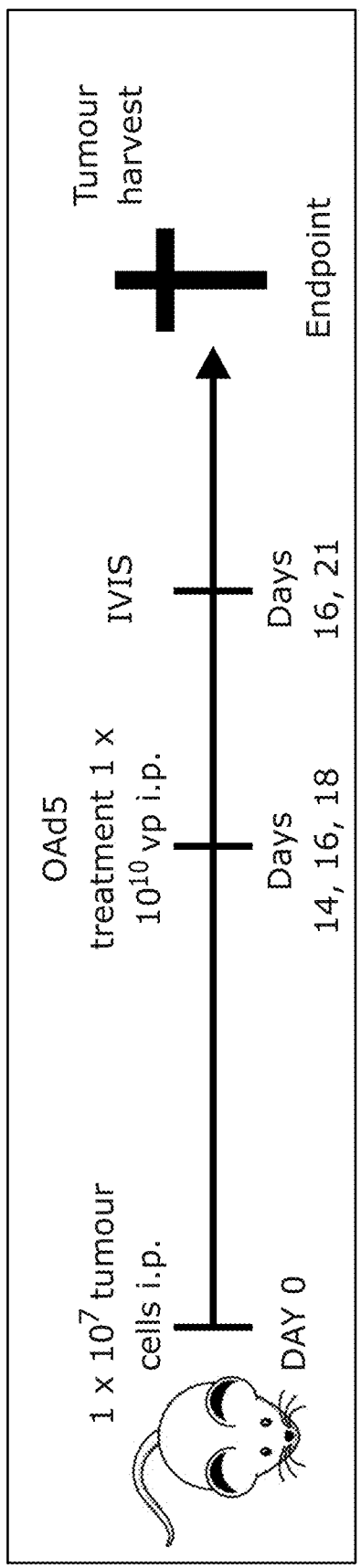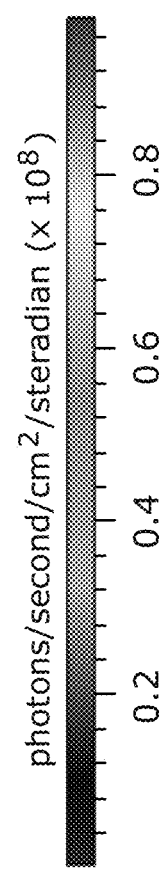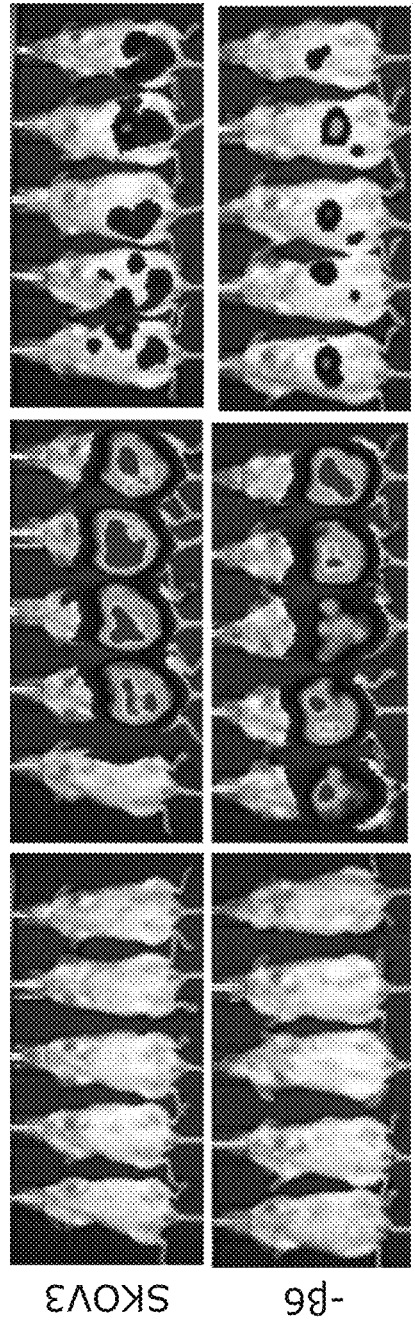

| Fold decrease in ex vivo luminescence vs. Ad5 group | | | | | |
|---|---|---|---|---|---|
| Group | Liver | Spleen | Lungs | Ovaries | Heart |
| Ad5.3D.A20 | 13 300 | 9230 | 3700 | 1100 | 573 |

FIG. 8D

SEQUENCE LISTING

```
<160> NUMBER OF SEQ ID NOS: 1

<210> SEQ ID NO 1
<211> LENGTH: 20
<212> TYPE: PRT
<213> ORGANISM: Foot-and-mouth disease virus

<400> SEQUENCE: 1

Asn Ala Val Pro Asn Leu Arg Gly Asp Leu Gln Val Leu Ala Gln Lys
1               5                   10                  15

Val Ala Arg Thr
            20
```

MODIFIED ADENOVIRUSES

This application is the national stage of international patent application no. PCT/GB2019/050380 filed on Feb. 13, 2019, which in turn claims priority from Great Britain Patent Application No. 1802539.5 filed on Feb. 16, 2019, the disclosures of which are incorporated herein by reference in their entirety.

REFERENCE TO SEQUENCE LISTING SUBMITTED ELECTRONICALLY

A sequence listing electronically submitted with the present application as an ASCII text file named 1776-065SequenceListingST25.txt, created on Aug. 13, 2020 and having a size of 550 bytes, is incorporated herein by reference in its entirety.

LENGTHY TABLES

The patent contains a lengthy table section. A copy of the table is available in electronic form from the USPTO web site (https://seqdata.uspto.gov/?pageRequest=docDetail&DocID=US12318418B2). An electronic copy of the table will also be available from the USPTO upon request and payment of the fee set forth in 37 CFR 1.19(b)(3).

TECHNICAL FIELD

The invention concerns a modified oncolytic adenovirus of serotype Ad5; a pharmaceutical composition comprising same; and a method of treating cancer using same wherein said modified adenovirus comprises at least one point mutation(s) in the hexon hypervariable region 7 (HVR7 mutation) to prevent virus binding with coagulation factor 10 (FX); at least one point mutation(s) in the fiber knob region AB loop (KO1 mutation) to prevent virus binding with the coxsackie and adenovirus receptor (CAR); and at least one point mutation(s) in the penton integrin binding motif Arg-Gly-Asp (RGD) to prevent virus binding with $\alpha V\beta 3/\alpha V\beta 5$ integrin.

BACKGROUND

Cancer virotherapy is a rapidly emerging field with herpes simplex type 1-based talimogene laherparepvec (T-VEC) as the first oncolytic immunotherapy for advanced melanoma. Oncolytic adenoviruses are highly immunogenic viruses often used in various vaccine approaches against infectious diseases. Importantly, they have an exceptional ability to both prime and boost immune responses. Further, the presence of an oncolytic adenovirus within a tumor and the immunogenic cell death it causes is likely to shape the hostile tumor microenvironment towards a more susceptible state for a clinically relevant anti-tumor immunity to occur, by causing the expression of TH1-type immune modulators such as IFNg. However, the immunogenicity of oncolytic adenoviruses is a double-edged sword; the anti-virus immunity is often so overwhelming, that it overrides the much weaker immune response evoked against self-antigens expressed by the tumor.

Adenovirus 5 (Ad5) is a common vector deployed in numerous clinical trials for cancer and gene therapies (clinicaltrials.gov, 2016) because it can be genetically manipulated and it tolerates large transgenes. However, this serotype has several suboptimal features that hamper its wider clinical use. Ad5 is a common respiratory virus, with seroprevalence rates close to 100% in certain populations—neutralising antibodies (nAbs) rapidly inactivate systemically delivered therapeutic vectors. Other suboptimal features include its extensive off-target sequestration to spleen and liver via bridging of the viral hexon protein and heparan sulphate proteoglycans (HSPGs), a tropism-dictating interaction mediated by human coagulation factor 10 (FX). In vitro, Ad5 enters host cells via interaction between viral fiber protein and coxsackie and adenovirus receptor (CAR) that is ubiquitously expressed within tight junctions on polarised epithelial cells but down-regulated in progressive cancers. Subsequently, Ad5 internalises in host cells via $\alpha v\beta 3/5$ integrins by clathrin-mediated endocytosis mediated by the viral penton base protein.

The perception of the role of oncolytic viruses in cancer treatment has changed dramatically during the last decade, as immunotherapy and the stimulation of the patient's own immune system to target and attack cancer has gained popularity. At the beginning of the century, oncolytic viruses were perceived as active agents in cancer treatment, acting solely through their inherent ability to lyse tumor cells via oncolysis. Recently, their use as cancer vaccines has gained interest, and their ability to release tumor antigens from cancer cells upon oncolysis for activating the immune system is recognised as an important characteristic in designing the ultimate immunotherapy against cancer.

Viral vectors are therefore becoming increasingly attractive in the clinical setting, however, clinical efficacy of the common serotype—Ad5—is hampered by poor tumour-specificity, extensive off-target delivery and inactivation by innate immunity, necessitating innovative manipulation strategies.

We herein disclose a modified adenoviral vector designed to overcome the above drawbacks.

SUMMARY

According to a first aspect of the invention there is provided a modified Ad5 serotype adenovirus comprising:
 a) at least one of I421G, T423N, E424S, E450Q or L426Y point mutation(s) in the hexon hypervariable region 7 (HVR7 mutation) wherein said mutation prevents virus binding with coagulation factor 10 (FX);
 b) at least one of S408E or P409A point mutation(s) in the fiber knob region AB loop (KO1 mutation) wherein said mutation prevents virus binding with the coxsackie and adenovirus receptor (CAR); and
 c) at least one of D342E or D342A point mutation(s) in the penton integrin binding motif Arg-Gly-Asp (RGD) wherein said mutation prevents virus binding with $\alpha_v\beta_3/\alpha_v\beta_5$ integrin.

The modified Ad5 serotype adenovirus according to the invention is advantageous as its ability to infect off-target tissues is severely compromised, indeed, it is prevented/inhibited from infecting liver and spleen and also its ability to infect cells of the body in a widespread manner is also compromised. Thus the modified adenovirus is compromised in terms of the tissue it can infect.

Adenoviruses are medium-sized (90-100 nm), nonenveloped (without an outer lipid bilayer) viruses with an icosahedral nucleocapsid containing a double stranded DNA genome. In humans, there are 57 accepted human adenovirus serotypes (Ad-1 to 57) classified into seven species (Human adenovirus A to G): A—12, 18, 31; B—3, 7, 11, 14, 16, 21, 34, 35, 50, 55; C—1, 2, 5, 6, 57; D—8, 9, 10, 13, 15, 17, 19, 20, 22, 23, 24, 25, 26, 27, 28, 29, 30, 32, 33, 36, 37, 38, 39, 42, 43, 44, 45, 46, 47, 48, 49, 51, 53, 54, 56; E—4; F—40, 41; and G—52. Accordingly, reference herein to Ad5 refers to Adenovirus serotype 5 belonging to the C-subclass of adenovirus.

As is known to those skilled in the art, Adenovirus virions are composed of non-enveloped icosahedral shaped capsids that surround the viral DNA-protein core complex. Hexon is the most abundant structural protein, with 240 copies of the trimeric molecule per capsid. Twelve copies of the hexon trimer form each of the 20 triangular facets of the capsid. A complex of penton base and fiber proteins seals the vertices of the capsid and facilitates attachment (fiber) and internalization (penton base) of the virus.

The hexon protein is highly conserved among the different adenovirus serotypes with the exception of nine hypervariable regions (HVRs). These HVRs reside in two distinct loops that form the exposed surface of the hexon protein, HVRs 1-6 lie within the DE1 loop and HVRs 7-9 are located within the FG1 loop.

Accordingly, reference herein to at least one mutation in HVR7 refers to a mutation in the hypervariable region 7. Specifically, said at least one HVR7 mutation prevents interaction with coagulation Factor X thereby limiting off-target sequestration of the modified adenovirus to the liver, and improved targeting to target cancer cells.

In a preferred embodiment, said at least one HVR7 mutation comprises at least one amino substitution mutation to prevent FX interaction selected from one or more of the group comprising: I421G, T423N, E424S, E450Q or L426Y. Most preferably, said at least one HVR7 mutation comprises additionally or alternatively at least one of I421G, T423N, E424S, and L426Y point mutations.

As is known to those skilled in the art, adenoviral vectors have a natural tropism that leads to a widespread distribution of the vector. Entry of group C adenoviruses, such as Ad5, into cells is thought to involve high affinity binding of the virus to the cell through interaction of the viral fiber protein with coxsackievirus-adenovirus receptor (CAR). Therefore, for the purpose of anti-cancer therapy, targeting of adenoviral vectors to specific tissues or cell types requires modification of the normal tropism of the vector to improve specificity.

Adenoviral infection commences with recognition of host cell receptors by means of specialised proteins on the viral surface i.e. the adenovirus fiber protein and in particular the globular carboxy-terminal domain of the adenovirus fiber protein, termed the carboxy-terminal knob domain. Accordingly, reference herein to a knob of an adenoviral fiber protein is reference to the globular carboxy-terminal domain of the adenovirus fiber protein.

Accordingly, reference to at least one KO1 mutation refers to at least one mutation in the fiber knob region AB loop. Specifically, said at least one KO1 mutation prevents virus binding to CAR. In a preferred embodiment, said at least one KO1 mutation comprises at least one point mutation to prevent CAR binding selected from one or more of the group comprising: S408E or P409A. Most preferably said point mutation comprises S408E and P409A point mutations.

Adenovirus penton base contains five Arg-Gly-Asp sequences and bind integrins alpha v beta 3 and alpha v beta 5 ($\alpha_v\beta3/\alpha_v\beta5$) to promote viral infection by permitting virus internalization. Through prevention of this interaction, we have found that off-site targeting to the spleen is reduced, thereby promoting tumour specific targeting, and moreover, there is a dampening release of pro-inflammatory cytokines that otherwise leads to adverse immune host response when used in the context of anti-cancer therapy.

Accordingly, reference to at least one RGD mutation refers to at least at least one mutation in the penton integrin binding motif Arg-Gly-Asp (RGD mutation) wherein said mutation prevents virus binding with $\alpha_v\beta3/\alpha_v\beta_5$ integrin. In a preferred embodiment, said at least one RGD mutation comprises at least one point mutation selected from one or more of the group comprising: D342E or D342A to produce RGE or RGA, respectively. Most preferably said point mutation is D342E to produce RGE.

In yet a further preferred embodiment said adenovirus is further modified to include at least one cancer targeting modification that selectively targets tumour cells, in particular, specific types of tumour cells. As will be appreciated by those skilled in the art, through incorporation of the mutations described herein to modify the natural tropism of the adenovirus and also the introduction of at least one targeting modification/sequence, said modified virus has improved tumour specificity and reduced off-site targeting thereby reducing unwanted side-effects. Examples of cancer targeting modifications/sequences are known to those in the art such as, but not limited to, NGR (containing) peptides to bind aminopeptidase N, in particular adenoviruses (Ads) bearing NGR in the HI loop of the adenoviral fiber protein; YSA (containing) peptides to bind to pan-cancer marker EphA2, in particular adenoviruses bearing YSA in the chimeric fiber, resulting in strong transduction of EphA2-positive but not EphA2-negative cancer cells; growth factor antibodies, in particular chemical linkage of these targeting moieties, e.g. bFGF, EGFR, antibodies (e.g. Cetuximab, Herceptin, Avastin or the like) to the adenovirus using e.g. avidin/biotin linkages; and matrix degrading enzymes which once attached (typically, chemically linked e.g. linkage via hyaluronidase) to the outside of the virus, degrade extracellular membrane and so enable the virus to more efficiently permeate into the tumour microenvironment.

In a preferred embodiment, said cancer targeting modification comprises insertion or expression of an $\alpha v\beta6$ integrin binding peptide (identified using conventional techniques, such as sequence binding and homology techniques) such as the A20 peptide sequence NAVPNLRGDLQVLAQKVART (SEQ ID NO: 1) into the virus or by the virus, respectively, and, ideally, into or in the viral fiber knob HI loop (this modified virus hereinafter is referred to as Ad5.3D.A20). A20 was originally derived from foot-and-mouth disease virus (FMDV) capsid protein VP1 and has a natively high affinity to $\alpha v\beta6$ integrin. $\alpha v\beta6$ integrin is expressed in a third of ovarian cancers and in a variety of other epithelial cancers and is non-detectable in healthy adult tissues. Therefore, as will be appreciated by those skilled in the art, through expression and incorporation of this sequence in the modified virus, the modified virus can selectively target $\alpha v\beta6$ integrin overexpressing cancers such as, but not limited to, ovarian cancer, pancreatic cancer, oesophageal cancer, lung cancer, cervical cancer, head and neck cancer, oral cancer, cancer of the larynx, skin cancer, breast cancer, kidney cancer, and colorectal cancer.

The skilled person will appreciate that homologues, orthologues or functional derivatives of the recited mutations will also find use in the context of the present invention. Thus, for instance mutations which include one or more additions, deletions, substitutions or the like are encompassed by the present invention. In addition, it may be possible to replace one amino acid with another of similar "type". For instance, replacing one hydrophobic amino acid with another one can be achieved by using a program such as the CLUSTAL program to compare amino acid sequences. This program compares amino acid sequences and finds the optimal alignment by inserting spaces in either sequence as appropriate. It is possible to calculate amino acid identity or similarity (identity means conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In yet a further preferred embodiment still, said modified adenovirus vector (Ad5.3D.A20) comprises:
a) at least one of I421G, T423N, E424S, E450Q or L426Y point mutation(s) in the hexon hypervariable region 7 (HVR7 mutation) wherein said mutation prevents virus binding with coagulation factor 10 (FX);
b) at least one of S408E or P409A point mutation(s) in the fiber knob region AB loop (KO1 mutation) wherein said mutation prevents virus binding with the coxsackie and adenovirus receptor (CAR);
c) at least one of D342E or D342A point mutation(s) in the penton integrin binding motif Arg-Gly-Asp (RGD) wherein said mutation prevents virus binding with $\alpha_v\beta_3/\alpha_v\beta_5$ integrin; and
d) insertion or expression of the A20 peptide sequence NAVPNLRGDLQVLAQKVART (SEQ ID NO: 1) in the viral fiber knob HI loop.

More preferably still said modified adenovirus vector (Ad5.3D.A20) comprises:
a) I421G, T423N, E424S, and L426Y point mutations in the hexon hypervariable region 7 (HVR7 mutation) wherein said mutation prevents virus binding with coagulation factor 10 (FX);
b) S408E and P409A point mutations in the fiber knob region AB loop (KO1 mutation) wherein said mutation prevents virus binding with the coxsackie and adenovirus receptor (CAR);
c) D342E point mutation in the penton integrin binding motif Arg-Gly-Asp (to produce RGE mutation) wherein said mutation prevents virus binding with αVβ3/αVβ5 integrin; and
d) insertion or expression of the A20 peptide sequence NAVPNLRGDLQVLAQKVART (SEQ ID NO: 1) in the viral fiber knob HI loop.

In the above viral vector of the invention we successfully ablated the native tropisms of Ad5 by mutating the main capsid proteins: hexon, fiber and penton. A triple de-targeted Ad5-based vector backbone was generated (Ad5.3D), with modifications in the hexon hypervariable region 7 (HVR7 mutation), fiber knob AB loop (KO1 mutation) and penton integrin-binding motif Arg-Gly-Asp (RGD mutation) with substitution mutations in amino acid residues responsible for binding to coagulation factor 10 (FX), coxsackie and adenovirus receptor (CAR), and αvβ3/5 integrins, respectively.

The Ad5.3D vector was generated using homologous recombination techniques and provided in a high viral titre using a complementary cell line engineered to rescue the compromised adenovirus. The combination of three tropism-ablation mutations completely blocked cell entry via αvβ3/5 integrins, CAR and FX in vitro. Further, as proof of principle, we further modified the adenovirus by incorporation of an additional targeting sequence to preferentially target and infect specific cancer tumour cells, namely αvβ6, by the genetic incorporation of a heterologous αvβ6 integrin-binding peptide (A20, NAVPNLRGDLQVLAQKVART; SEQ ID NO: 1) within the viral fiber knob HI loop (Ad5.3D.A20). The Ad5.3D.A20 adenovirus was propagated using 296-β6 cells which were engineered to overexpress β6.

αvβ6 integrin is expressed in a third of ovarian cancers and in a variety of other epithelial cancers and is non-detectable in healthy adult tissues. Ad5.3D.A20 efficiently transduced αvβ6+ ovarian cancer cell lines and primary clinical ascites-derived EOC ex vivo cultures, even in the presence of highly neutralising ascites. In vivo biodistribution profile of Ad5.3D.A20 following systemic delivery in non-tumour-bearing mice was remarkably altered compared to Ad5, with reduced luciferase expression in all off-target organs and 7-log reduced viral genome load in the liver. Further, anti-tumour efficacy of oncolytic Ad5.3D.A20 (OAd5.3D.A20) following intraperitoneal delivery was assessed in immunocompromised mice bearing intraperitoneal SKOV3(-β6) EOC xenografts. Oncolytic treatment with OAd5.3D.A20 improved overall survival as compared to Ad5 treatment.

Accordingly, Ad5.3D modified adenovirus is a viral vector which, through incorporation of a further cancer specific targeting mutation, represents an exciting targeting platform for cancer treatment and adenovirotherapy.

In yet a further preferred embodiment still, said adenovirus is further modified to include at least one transgene encoding a molecule or agent such as, but not limited to, a therapeutic agent. This embodiment therefore concerns the delivery of an agent, intracellularly, to exert a therapeutic action on the targeted cancer cell. Examples of an agent may include an agent that directly stimulates an immune responses, for example GM-CSF, IL-12; an agent to indirectly stimulate the immune system, e.g. an antibody (or fragments of an antibody) encoding an immune checkpoint inhibitor to inhibit a co-repressor such as CTLA-4, PD-L1, PD1, or Lag3; a Bi-specific T cell Engaging (BiTE) antibody construct; a Bi-specific natural killer cell engaging (BiKE) antibody construct; an agents that sensitises tumours to a cell based immunotherapy e.g. encoding CD19; an agents that depletes regulatory T cells within the tumour microenvironments. encoding anti-CD25 antibodies; an agents that sensitises a tumour to radiotherapy or for imaging e.g. by encoding sodium/iodide symporter (NIS) or somatostatin receptor type 2 (SSTR2)). Alternatively, the transgene may encode a therapeutic agent that is directly toxic to a tumour cell, e.g. by encoding the transgene Reduced Expression in Immortalized Cells (REIC/DKK3), or an enzyme that sensitises a cancer cell via conversion of a non-toxic prodrug into a toxic drug e.g. cytosine deaminase, nitroreductase, thymidine kinase. Other transgenes known in the art and useful in the treatment of cancer may be used in the working of the invention.

In yet a further preferred embodiment still, said adenovirus is further modified to include a 24-base pair deletion dl922-947 (Δ24 mutation) in the E1A gene to restrict viral replication to pRB-defective cells.

Yet more preferably still, said adenovirus is further modified to include a single adenine base addition at position 445 within the endoplasmic reticulum (ER) retention domain in E3/19K (T1 mutation) for enhanced oncolytic potency.

According to a second aspect of the invention there is provided the modified adenovirus as defined herein for use as a medicament.

According to a third aspect of the invention there is provided the modified adenovirus as defined herein for use in the treatment of cancer.

According to a fourth aspect of the invention there is provided a modified adenovirus as defined herein for use in the manufacture of a medicament to treat cancer.

Most preferably the cancer referred to herein includes any one or more of the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

Compounds for use in medicine will generally be provided in a pharmaceutical or veterinary composition and therefore according to a yet fifth aspect of the invention there is provided a pharmaceutical composition comprising the adenovirus as defined herein and a pharmaceutically acceptable carrier, adjuvant, diluent or excipient.

Suitable pharmaceutical excipients are well known to those of skill in the art. Pharmaceutical compositions may be formulated for administration by any suitable route, for example oral, buccal, nasal or bronchial (inhaled), transdermal or parenteral and may be prepared by any methods well known in the art of pharmacy.

The composition may be prepared by bringing into association the above defined adenovirus with the carrier. In general, the formulations are prepared by uniformly and intimately bringing into association the adenovirus with liquid carriers or finely divided solid carriers or both, and then if necessary shaping the product. The invention extends to methods for preparing a pharmaceutical composition comprising bringing an adenovirus as defined above in conjunction or association with a pharmaceutically or veterinary acceptable carrier or vehicle.

According to an even further aspect of the invention, there is provided a method for treating cancer comprising administering an effective amount of the modified adenovirus or pharmaceutical composition as defined herein to a patient in need thereof.

Reference herein to an "effective amount" of the adenovirus or a composition comprising same is one that is sufficient to achieve a desired biological effect, such as cancer cell death. It is understood that the effective dosage will be dependent upon the age, sex, health, and weight of the recipient, kind of concurrent treatment, if any, frequency of treatment, and the nature of the effect desired. Typically, the effective amount is determined by those administering the treatment.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWING FIGURES

An embodiment of the present invention will now be described by way of example only with reference to the following wherein:

FIG. 1. Generated vectors. (A) Viral titres and expected tropisms of Ad5 and triply detargeted, αvβ6 integrin retargeted vector, Ad5.3D.A20. (B) Vector map of the oncolytic Ad5.3D.A20. (C) Comparative predictive 3D modelling of the adenovirus serotype 5 (Ad5) fiber knob and of the modified Ad5.3D.A20 fiber knob with A20 peptide (NAVPNLRGDLQVLAQKVART; SEQ ID NO: 1) insertion in HI loop (in green). CAR, coxsackie and adenovirus receptor; FX, coagulation factor 10; HVR7, FX-binding mutation in hexon hypervariable region 7; KO1, CAR-binding mutation in fiber knob AB loop; Luc, luciferase transgene; vp, viral particle.

FIG. 2. Ablation of native receptor tropisms. (A) Binding of replication-deficient Ad5 and Ad5.3D.A20 vectors to coxsackie and adenovirus receptor (CAR). Ratio of viral transgene expression from Ad5.3D.A20 relative to Ad5 is indicated above bars. (B) Binding of replication-deficient Ad5 and HVR7-mutated Ad5 variant to coagulation factor 10 (FX0 was assessed in luciferase assays by infecting cells in the presence of human FX with (+) or without (−) anticoagulant X-bp for 3 h at 37° C. HVR7, FX-binding mutation. Statistical significance: ns, $p?0.05$; **, $p<0.01$.

FIG. 3. In vitro assessment of $\alpha v \beta 6$ integrin-targeting. Transduction efficiency of replication-deficient wild-type (Ad5) and triply-detargeted, integrin re-targeted (Ad5.3D.A20) vectors in (A) $\alpha v \beta 6+$ BT-20 breast cancer cells and (B) $\alpha v \beta 6+$ primary epithelial ovarian cancer (EOC) cells from patient 004. (C) Luciferase expression by oncolytic vectors (T1/$\Delta$24) in infected $\alpha v \beta 6$-low/CAR+ SKOV3 and $\alpha v \beta 6$-high/CAR+ SKOV3-$\beta 6$ cells (in-house produced SKOV3 cells with retroviral expression of $\alpha v \beta 6$). (D) Competition inhibition of $\alpha v \beta 6$ integrin-mediated cell entry. The highest 10% $\alpha v \beta 6$-expressing SKOV3-$\beta 6$ cells were sorted by FACS, sub-cultured and infected. IgG, normal mouse IgG control; 10D5, anti-$\alpha v \beta 6$ function-blocking antibody. Ratio of viral transgene expression is indicated above bars. Statistical significance ns, $p>0.05$; *, $p<0.05$; , $p<0.01$; *, $p<0.001$; ****, $p<0.0001$.

FIG. 4. The effect of malignant ovarian ascites on vector transduction ex vivo. (A) Quantification of anti-Ad5 antibodies in twenty clinical ovarian ascites (OAS) samples and control serum from a healthy male volunteer (solid black line) by ELISA. Horizontal lines indicate 50% and 100% binding of anti-Ad5 abs in the control serum. (B) Antigen specificity of anti-Ad5 antibodies in ascites and serum by Western blot. Vector transduction efficiency of replication-defective (Ad5) and Ad5.3D.A20 vectors, in the absence and presence of varying dilutions of ascites from an ovarian cancer patient 004 in (C) BT-20 cells and (D) primary ex vivo culture of epithelial ovarian cancer cells from patient 004. Cells were pre-incubated with ascending concentrations of ascites and infected.

FIG. 5. Biodistribution of replication-defective vectors at 72 h following systemic delivery. (A) Biodistribution study schedule and (B) in vivo imaging of biodistribution of replication-defective (Ad5) and triply-detargeted Ad5.3D.A20 virus, 3 days after intravenous injection. Quantitation of total luminescence signal from panel B: in (C) whole body, (D) liver, 335 (E) spleen, (F) lungs, (G) ovaries and (H) heart. i.p., intraperitoneal; IVIS, in vivo imaging system; p.i., post-infection; vp, viral particle. Error bars represent standard error of the mean; n=5/group; ns, $p>0.05$; *, $p<0.05$; , $p<0.01$; *, $p<0.001$; ****, $p<0.0001$.

FIG. 6. Viral genome copy number in off-target organs following systemic delivery. Adenovirus genome copy number from tissues excised in FIG. 5: (A) liver, (B) spleen, (C) lungs, (D) ovaries and (E) heart by qPCR for the hexon gene following systemic vector delivery. Data were normalised and analysed by one-way ANOVA and Sidak's multiple comparisons post hoc test in GraphPad Prism. Error bars represent standard error of the mean; n=5/group; *, $p<0.05$; , $p<0.01$; *, $p<0.001$; $p<0.0001$; ns, no statistically significant difference. Numbers below graphs indicate fold decrease of the Ad5.3D.A20 group relative to the Ad5 group.

FIG. 7. Oncolytic efficacy study: intraperitoneal delivery of oncolytic vectors in ovarian cancer xenograft model. (A) Study schedule. Intraperitoneal xenografts of human ovarian cancer cells (SKOV3 and SKOV3-16) were implanted into immune-compromised mice (n=5/group), then treated with 3 doses of intravenous oncolytic Ad5 or triply de-targeted, integrin re-targeted Ad5.3D.A20, on days 14, 16 and 18. Luminescence heat map images (B,D) and quantitation of total body luminescence (C, E) were determined at 349 48 h after the first treatment (Day 16), and at 7 days after the first treatment (Day 21). Overall survival of animals inoculated with SKOV3 ($\alpha v \beta 6$-low/CAR+) (F).

Figure 8A:
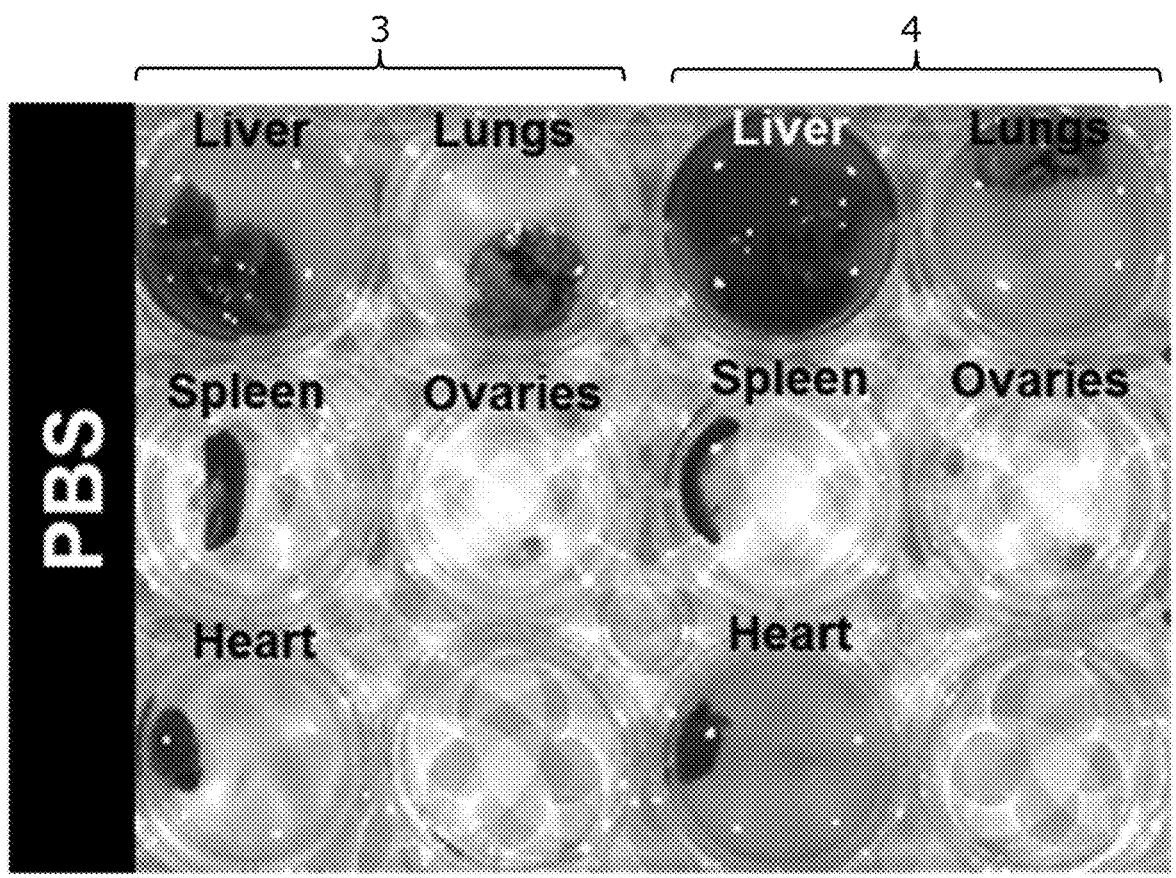
Figure 8B:
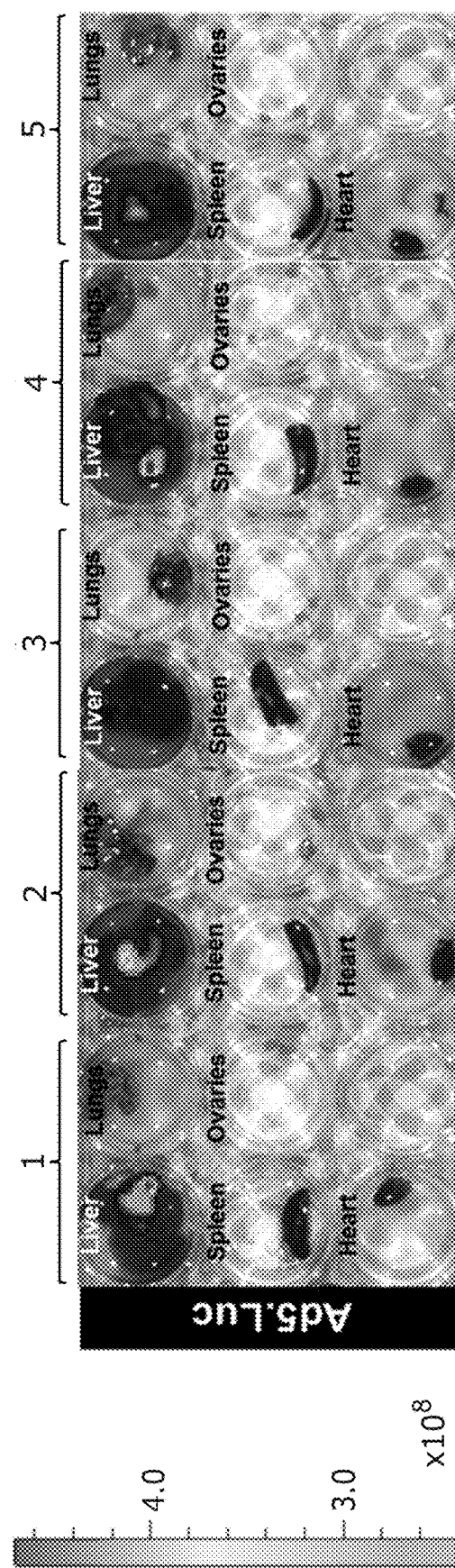
Figure 8C:
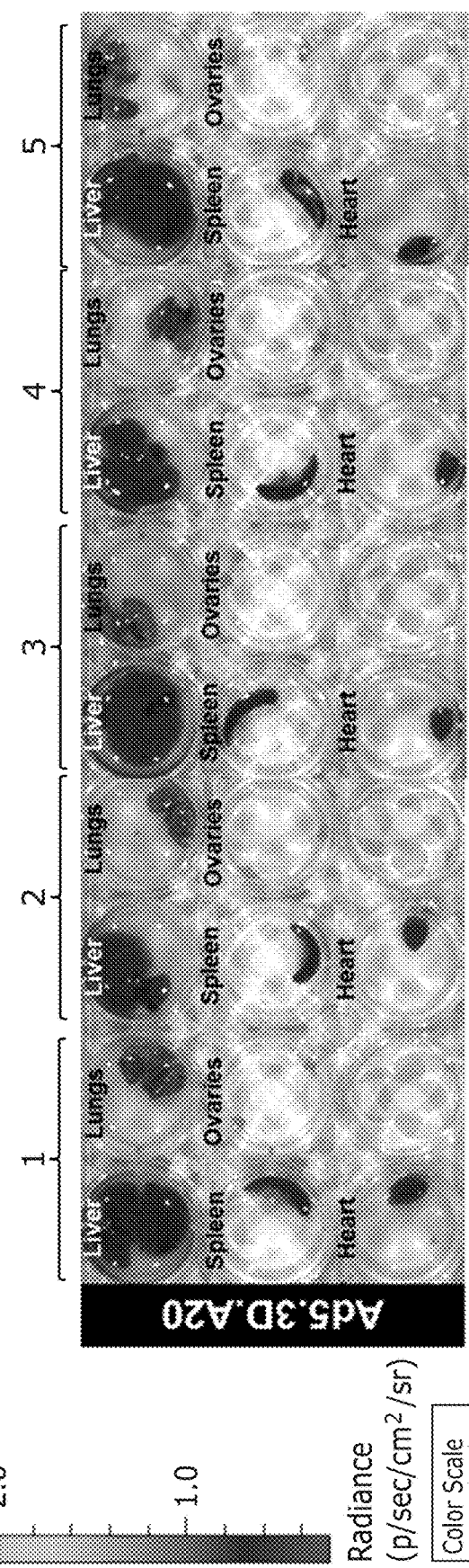

FIG. 8. Biodistribution study: Heat-map images of luminescence intensity ex vivo. Liver, spleen, lungs, ovaries and heart were collected immediately post-mortem from animals that had been intravenously inoculated with (A) PBS (control), (B) Ad5.Luc or (C) Ad5.3D.A20 vectors. Organs were immersed in D-luciferin and imaged in IVIS imager. The colour of the tissue indicates the relative luminescence intensity emitted by luciferase transgene; scales were normalised to exclude background luminescence. (D) Fold decrease in total luminescence (photons/second) relative to Ad5.Luc. The mean luminescence intensity of the Ad5.Luc group was divided by the mean luminescence in each organ in the Ad5.3D.A20 group. The mean value of the PBS control group was subtracted from all values.

FIG. 9. Biodistribution study: Immunohistochemistry on formalin-fixed, paraffin-embedded liver sections. (A) Haematoxylin-eosin staining for the visualisation of cellular structures, and mouse liver staining using a rabbit IgG isotype control antibody (1 μg/mL), a primary rabbit anti-CAR antibody (1:100) and a primary rabbit anti-ITGB6 ($\alpha v \beta 6$) antibody (1:10). (B) Staining of Ad5-infected liver cells in animals infected with Ad5 or Ad5.3D.A20 vectors, using a primary rabbit anti-Ad5 antibody (1 μg/mL). DAB was used as a substrate, sections counterstained in haematoxylin, mounted on coverslips and observed under a light microscope.

Figure 10A:
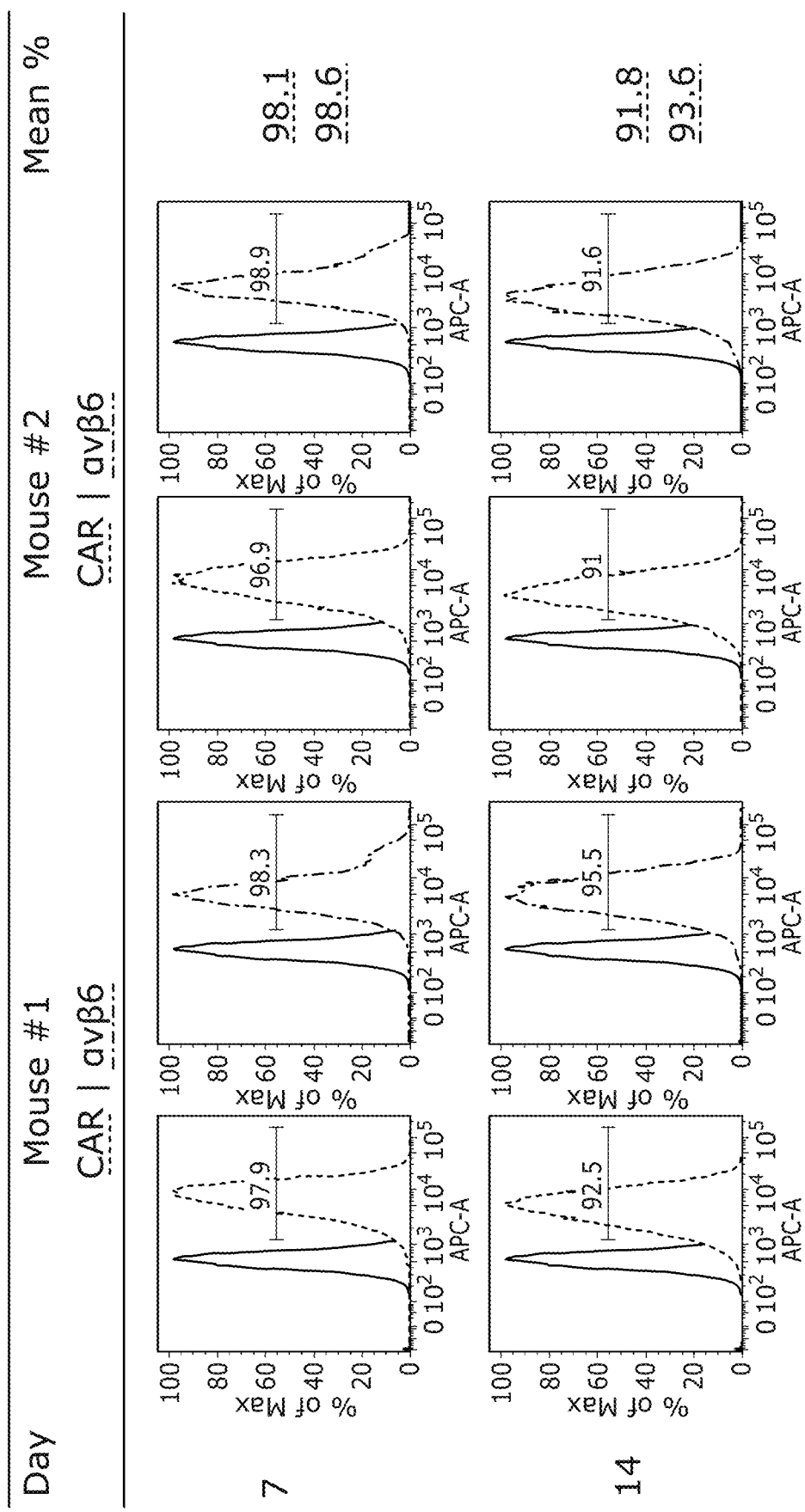
Figure 10B:
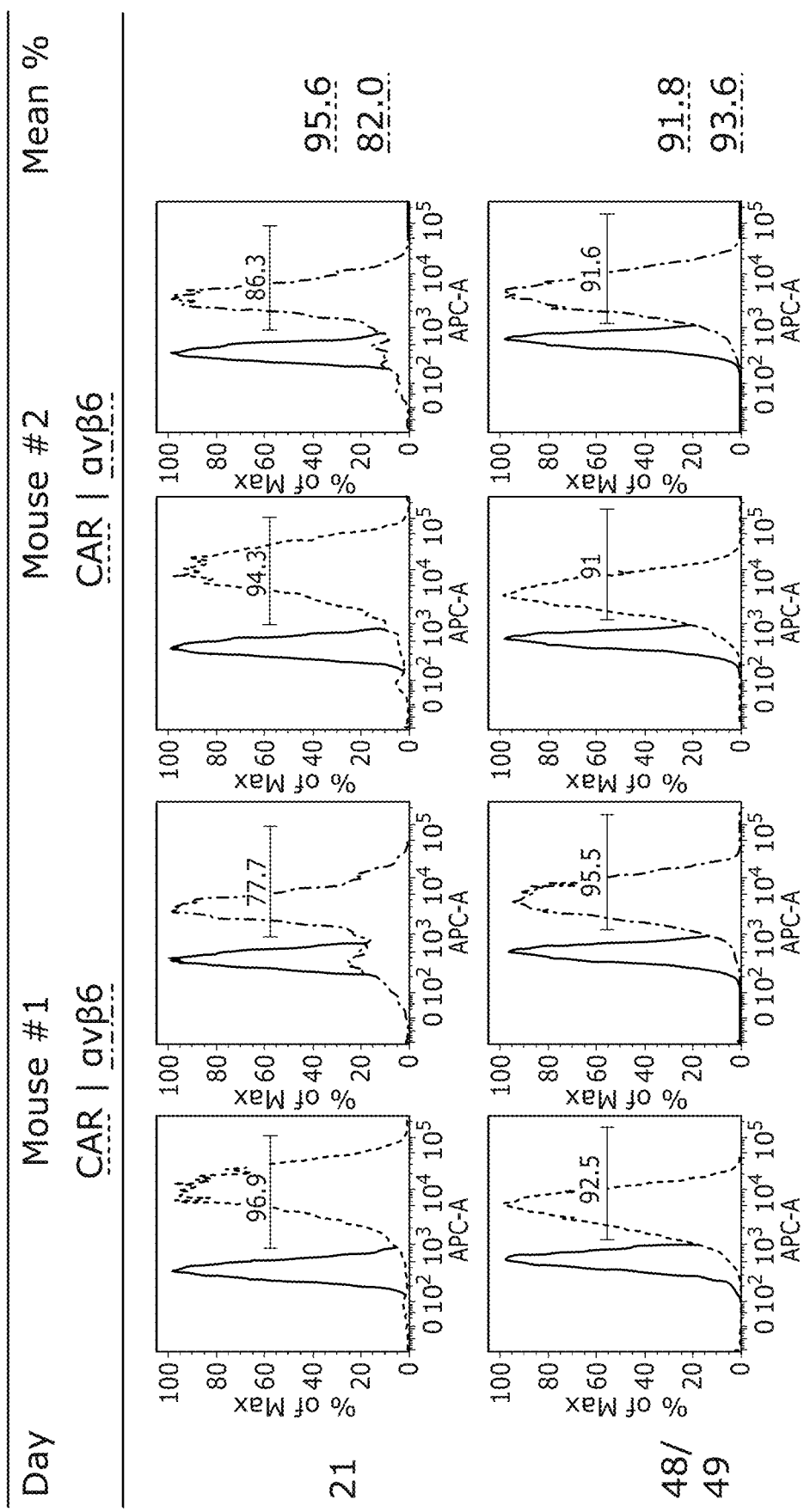

FIG. 10. Pilot study: Tumour localisation and take rate in NOD/SCID mice. $1 \times 10^7$ of SKOV3-$\beta 6$ cells/animal were implanted i.p. on day 0, and two mice sacrificed on each time-point: on day 7, 14 (A), 21 and 48/49 (final endpoint) (B). The approximate tumour size was measured, and the volume of ascites quantified.

Figure 11A:
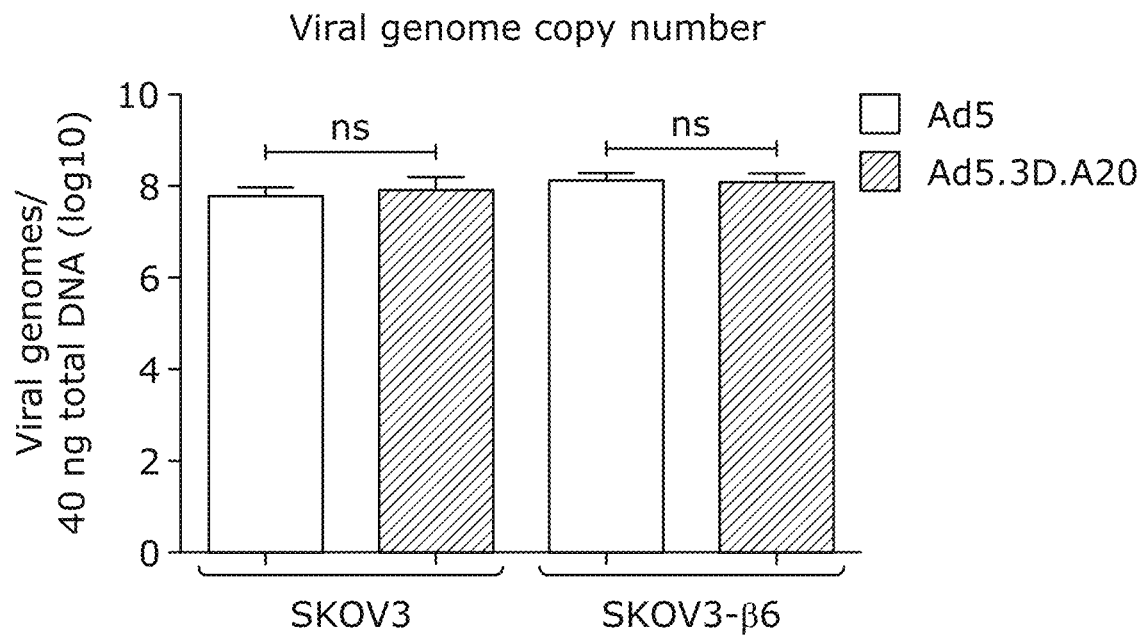
Figure 11B:
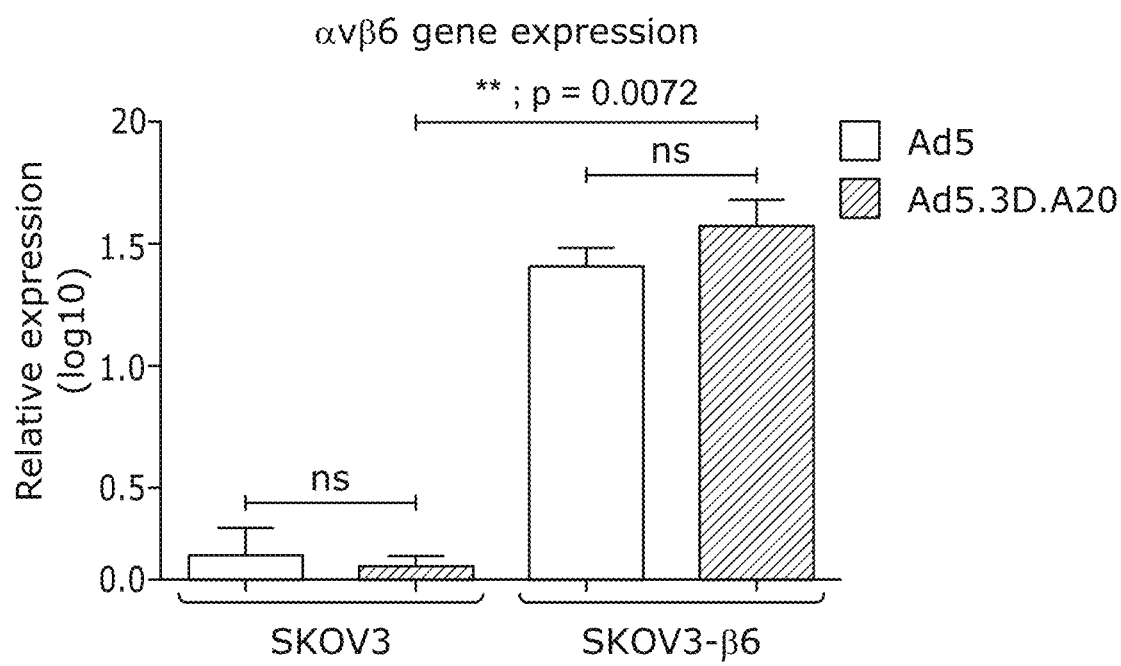
Figure 12A:
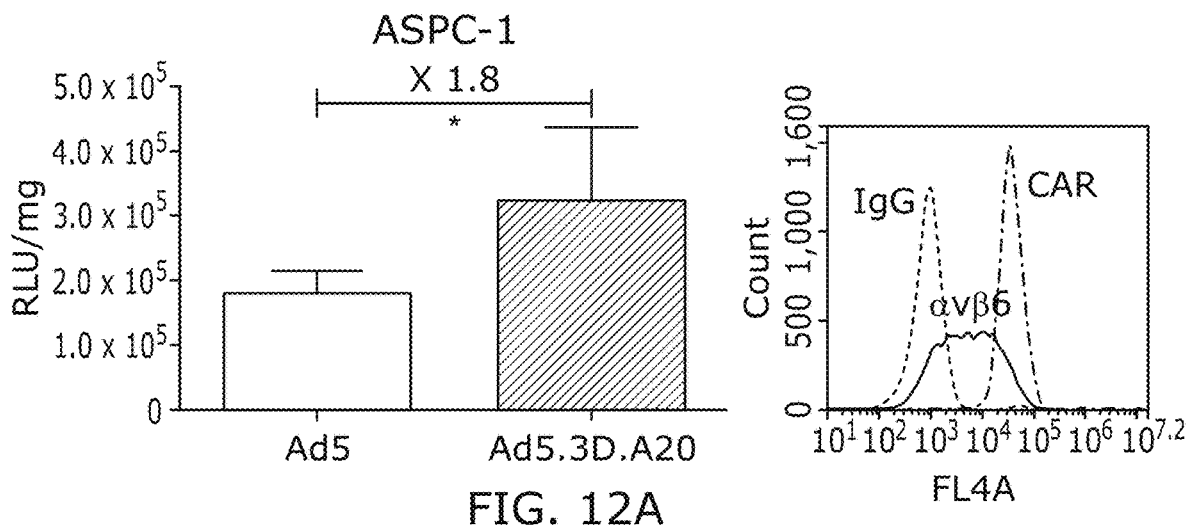
Figure 12B:
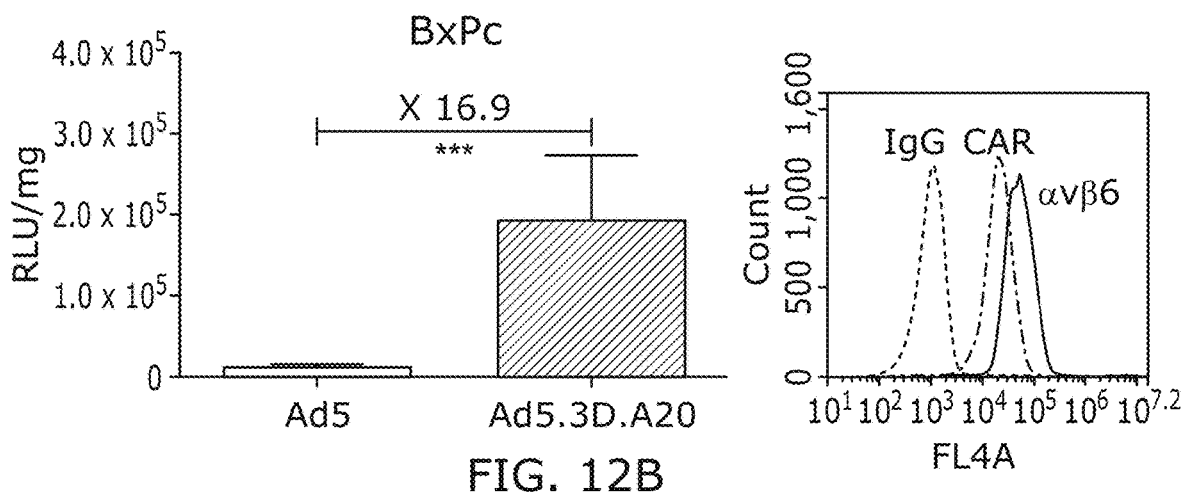
Figure 12C:
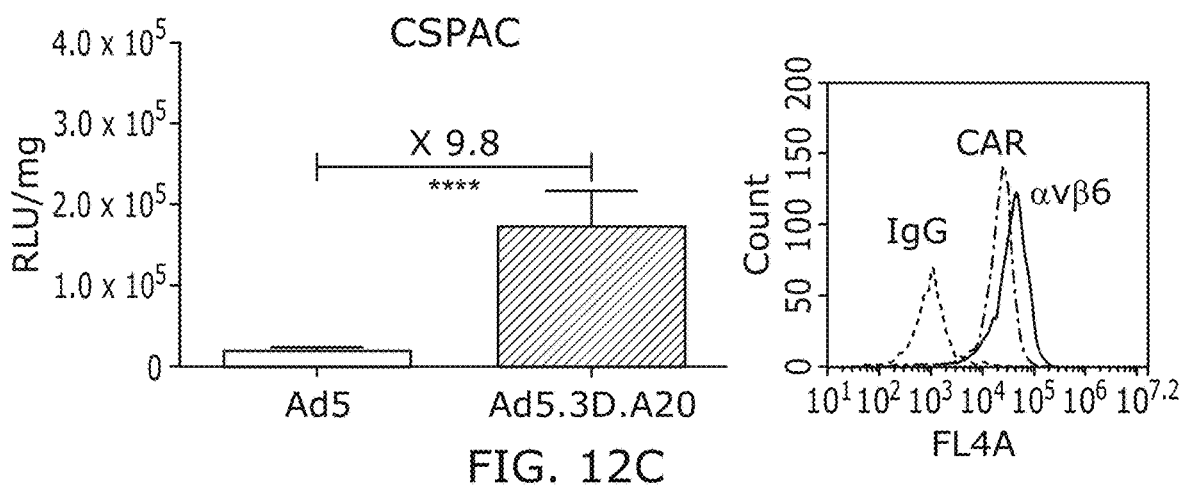
Figure 12D:
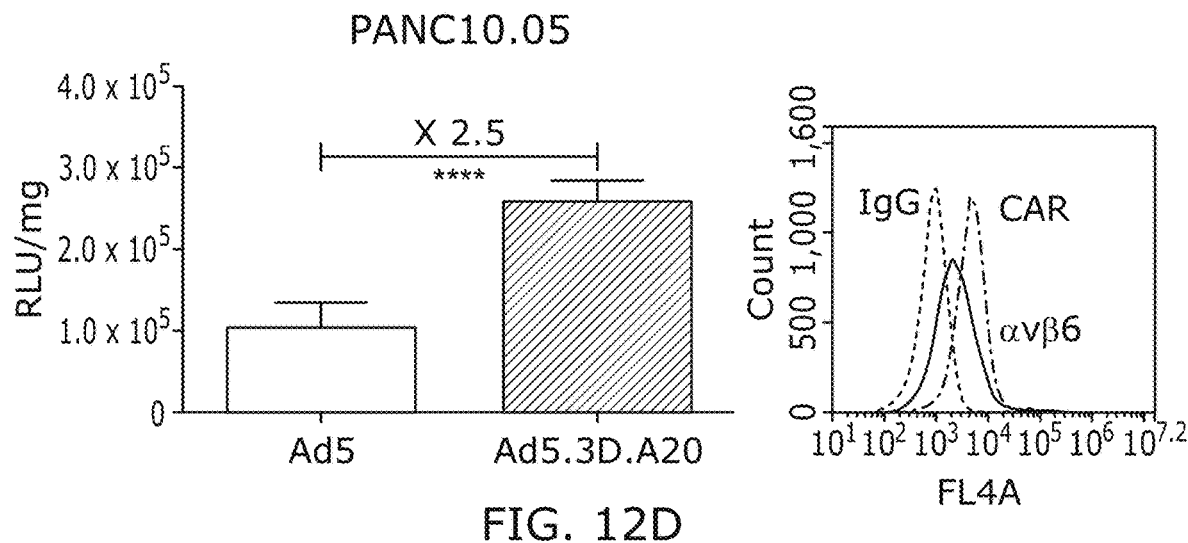
Figure 12E:
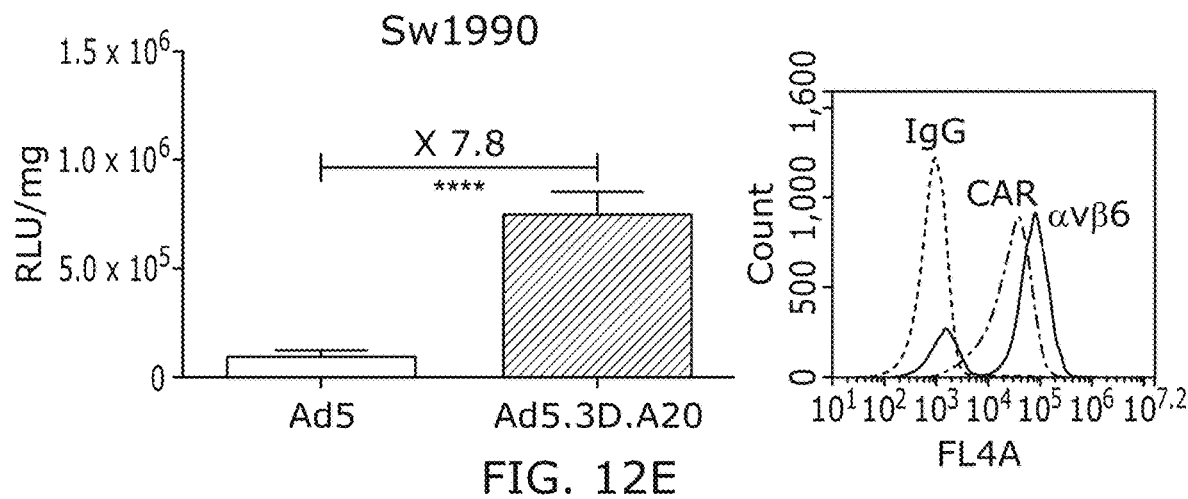
Figure 12F:
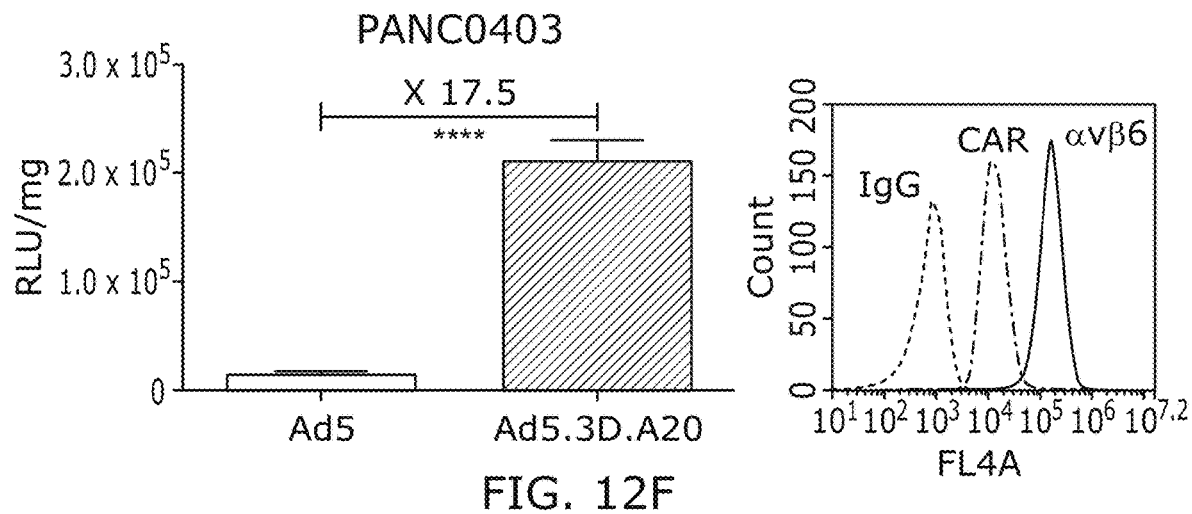
Figure 12G:
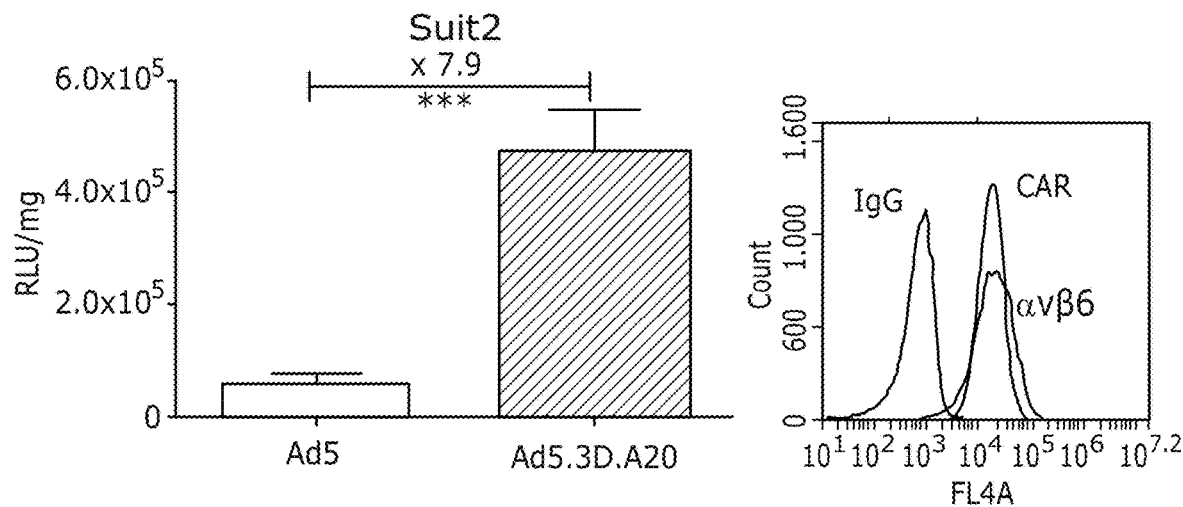
Figure 12H:
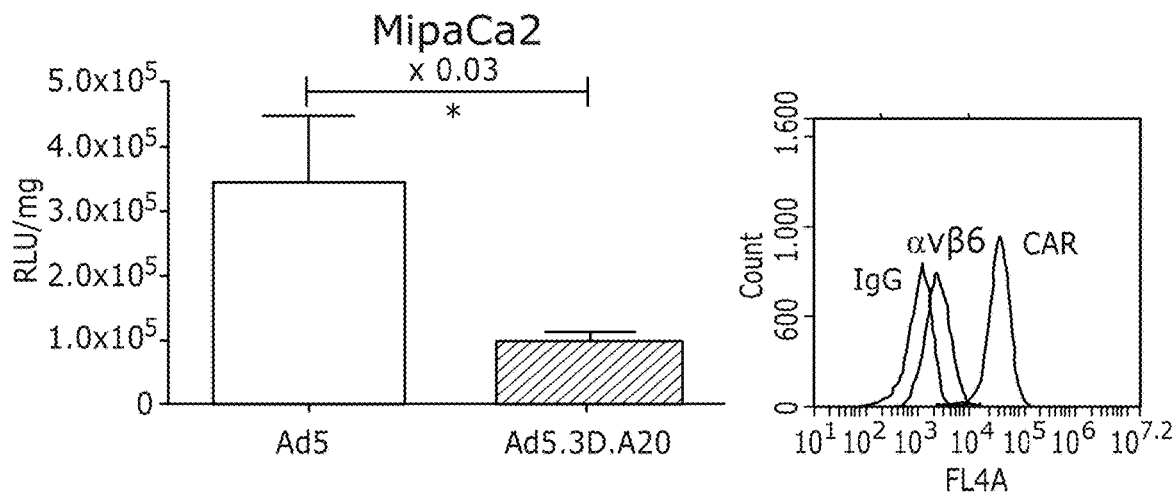
Figure 12I:
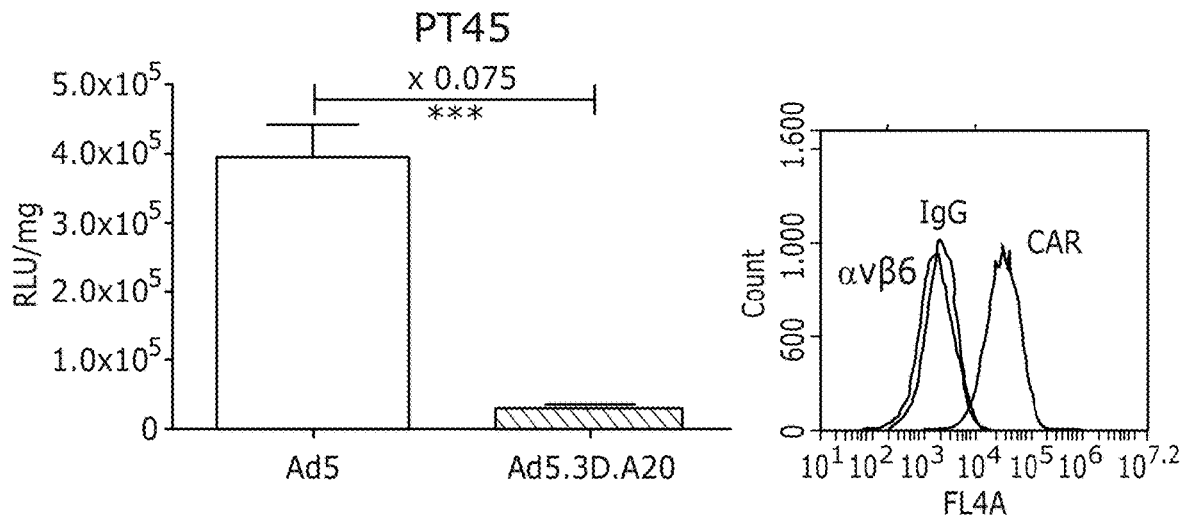

FIG. 11. Oncolytic efficacy study: Characterisation of endpoint tumours. (A) Viral genome copy number (per 40 ng of DNA) and (B) $\alpha v \beta 6$ integrin (ITGB6) gene expression in post-mortem tumours in OAd5 and OAd5.3D.A20 from SKOV3 and SKOV3-$\beta 6$ cohorts by qPCR. The level of $\alpha v \beta 6$ expression is shown relative to mouse #1 from the negative control PBS group in the SKOV3 cohort, by using human ACTB ($\beta$-actin) as an endogenous control.

FIG. 12. Transduction activity of Ad5.3D.A20 and Ad5 expressing luciferase in pancreatic cancer cell lines. Expression levels of $\alpha v \beta 6$ and hCAR were determined on ASPC-1 (A), BxPc (B), CFPAC (C), PANC10-05 (D), SW1990 (E), PANC0403 (F), SUIT-2 (G), MiPaCa2 (H) and PT45 (I) pancreatic cancer cell lines. Cells were infected with 5,000 vp/cell of virus expressing luciferase, and transgene expression quantified and corrected for total cellular protein 48 hours post infection.

Figure 13:
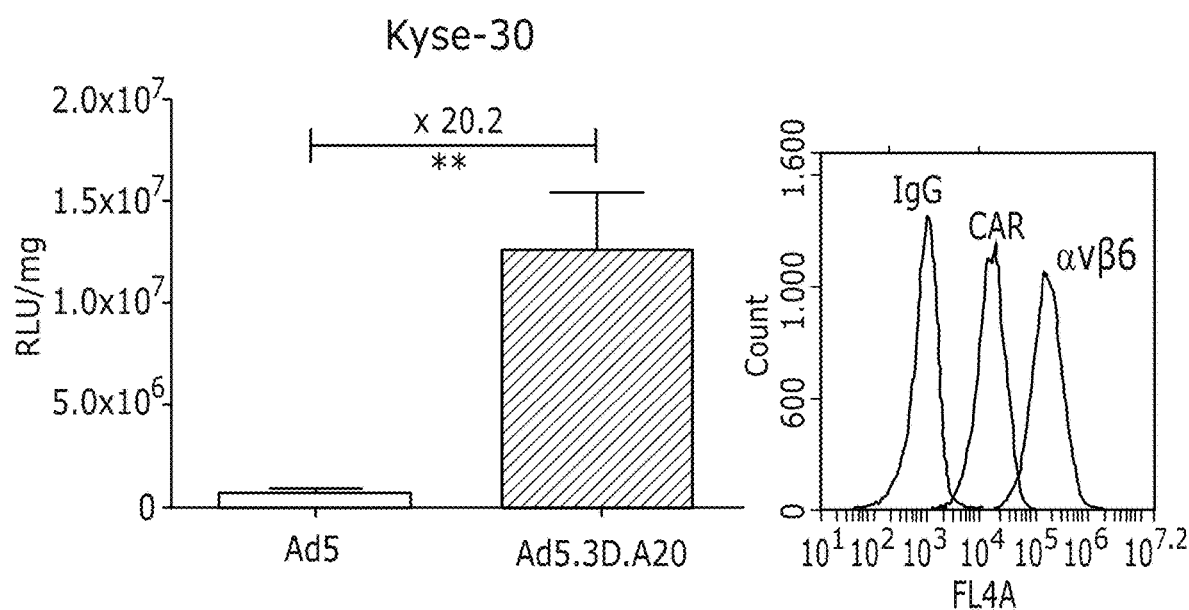

FIG. 13. Transduction activity of Ad5.3D.A20 and Ad5 expressing luciferase in oesophageal cancer cell lines. Expression levels of $\alpha v \beta 6$ and hCAR were determined on Kyse-30 oesophageal cancer cells. Cells were infected with 5,000 vp/cell of virus expressing luciferase, and transgene expression quantified and corrected for total cellular protein 48 hours post infection.

FIG. 14: transduction activity of Ad5.3D.A20 and Ad5 expressing luciferase in breast cancer cell lines. Expression levels of αvβ6 and hCAR were determined on BT-20 (A), BT-474 (B), MDA-MB-361 (C) and MDA-MB-231 (D) breast cancer cells. Cells were infected with 5,000 vp/cell of virus expressing luciferase, and transgene expression quantified and corrected for total cellular protein 48 hours post infection.

Figure 15A:
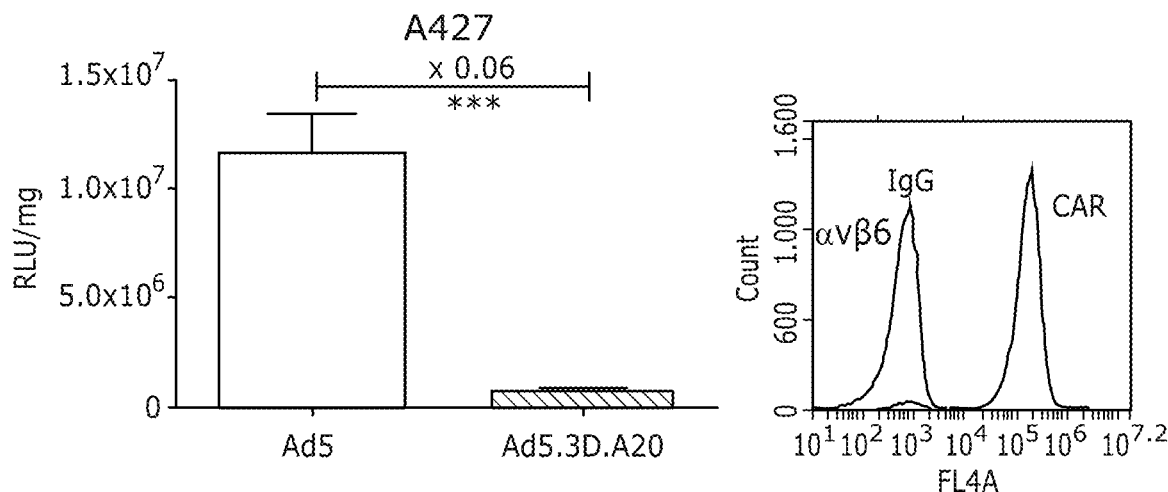
Figure 15B:
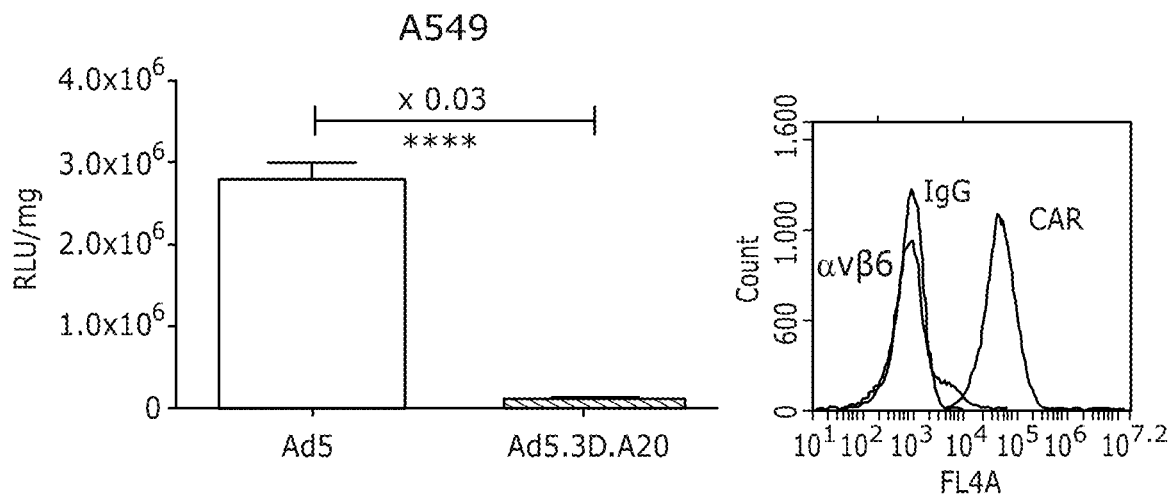
Figure 15C:
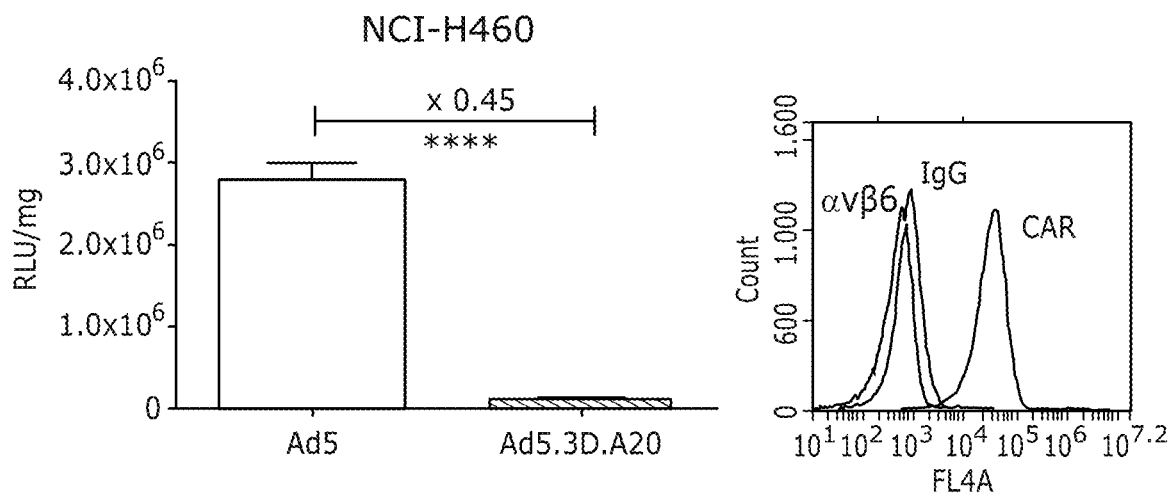
Figure 16A:
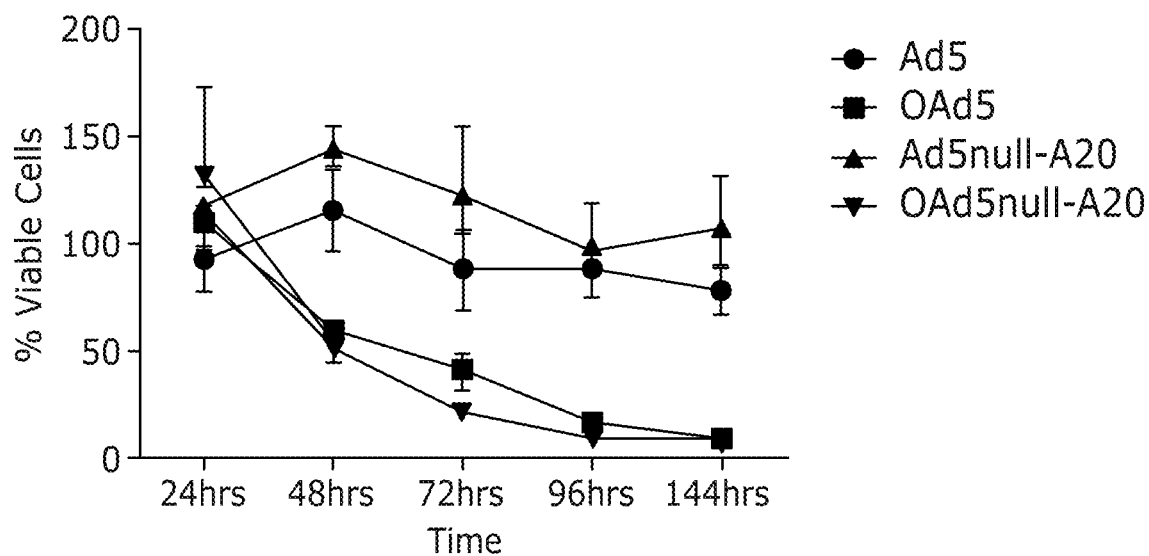
Figure 16A:
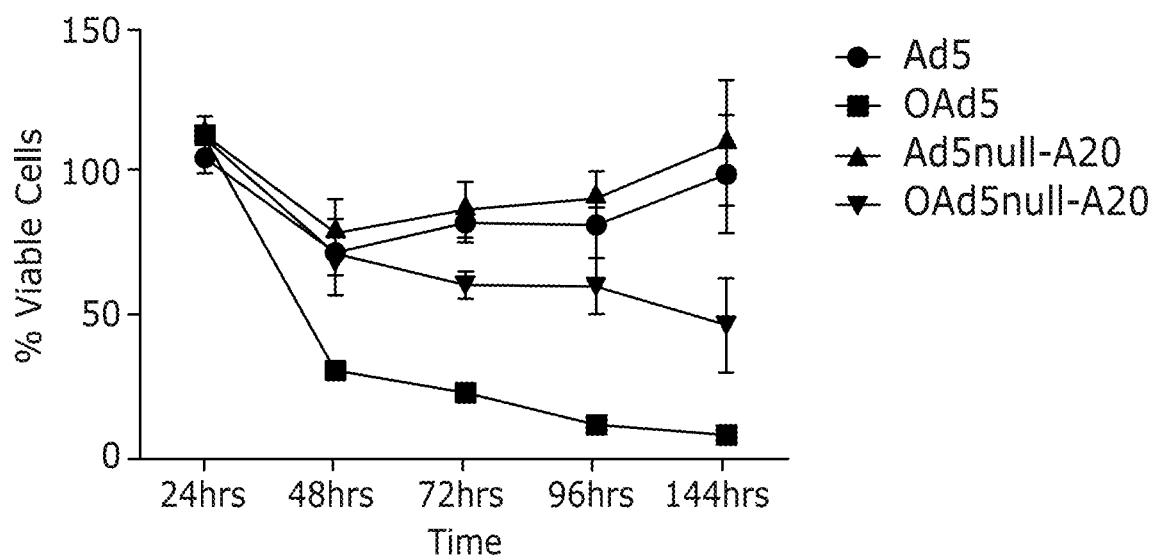
Figure 16B:
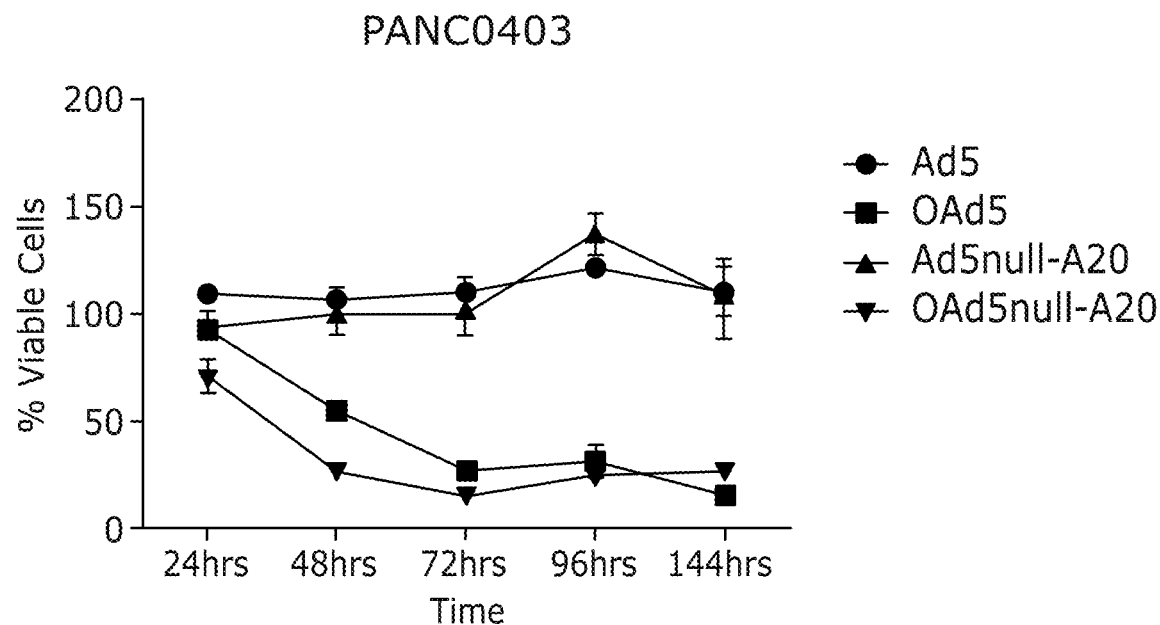
Figure 16B:
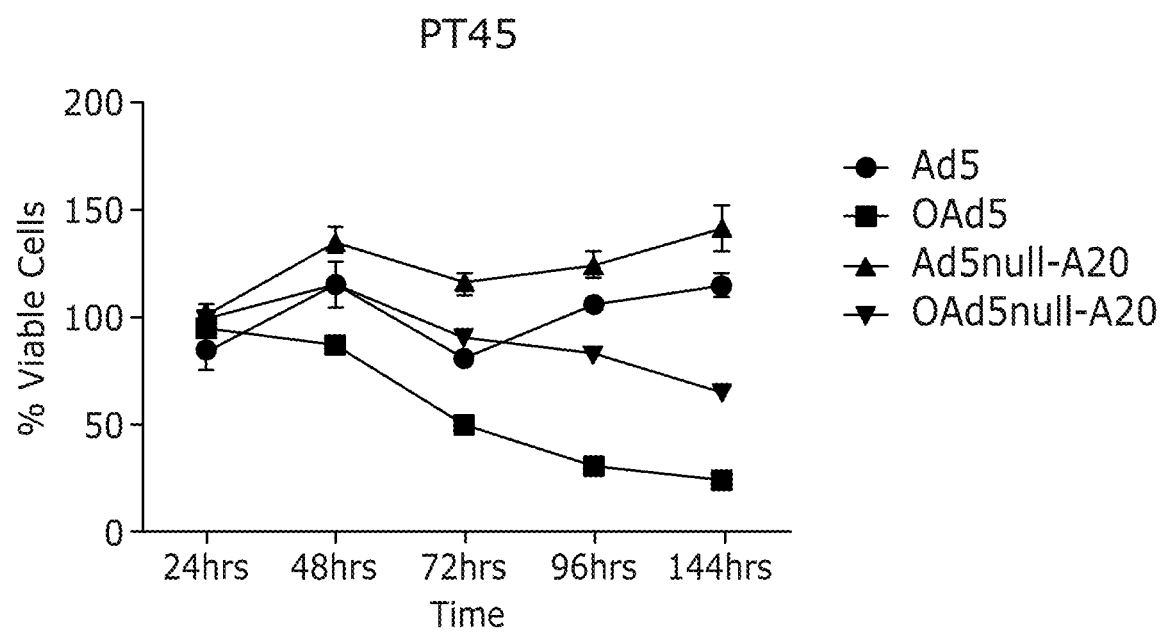
Figure 16C:
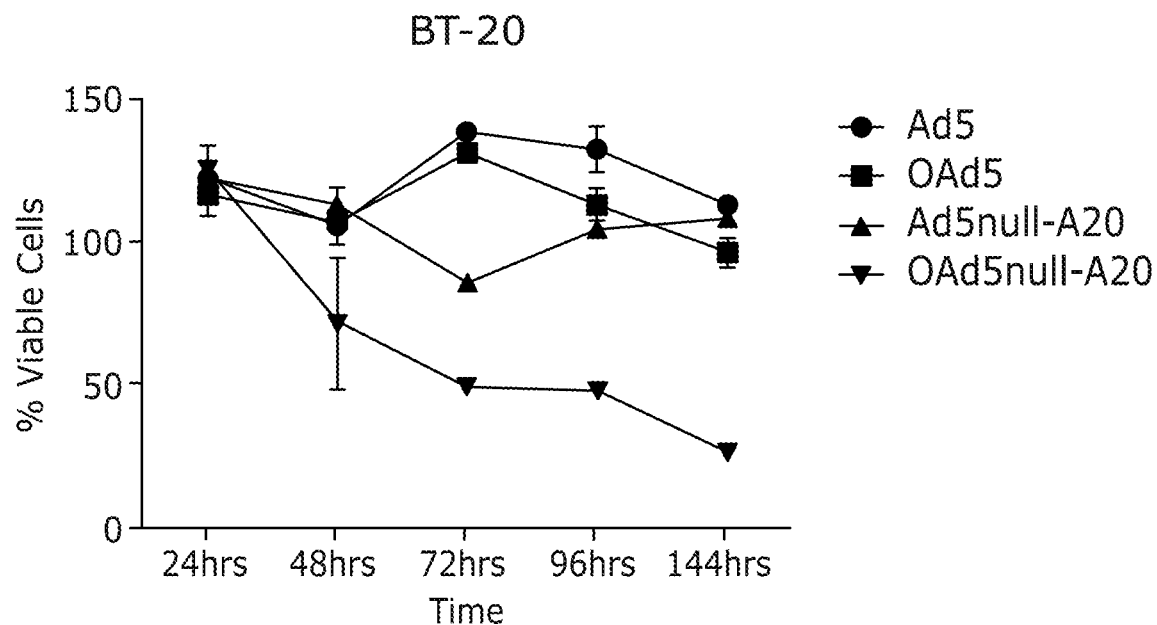
Figure 16C:
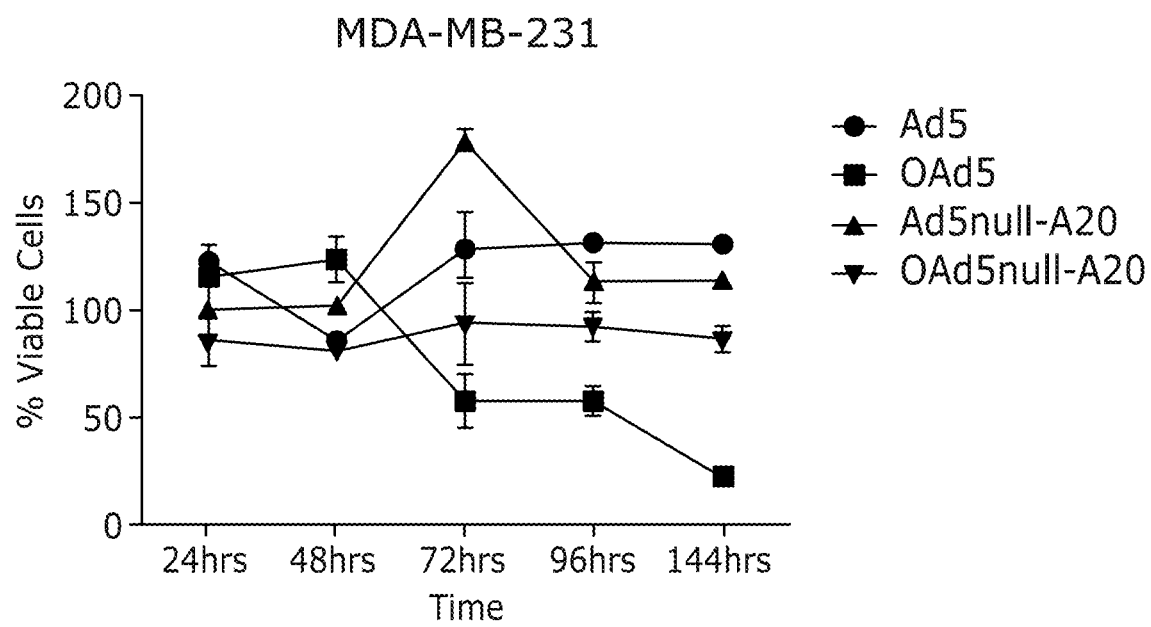

FIG. 15: transduction activity of Ad5.3D.A20 and Ad5 expressing luciferase in lung cancer cell lines. Expression levels of αvβ6 and hCAR were determined on A427 (A), A549 (B), and NCI-H460 (C) lung cancer cells. Cells were infected with 5,000 vp/cell of virus expressing luciferase, and transgene expression quantified and corrected for total cellular protein 48 hours post infection.

FIG. 16: oncolytic activity of replication deficient and oncolytic (O) Ad5.3D.A20 and Ad5 in pancreatic and breast cancer cell lines. The pancreatic cancer cell lines Suit 2 ($αvβ6^{high}$/$hCAR^{high}$), MiCaPa2 ($αvβ6^{low}$/$hCAR^{high}$) (A), PANC0403 ($αvβ6^{vhigh}$/$hCAR^{high}$) and PT45 ($αvβ6^{neg}$/$hCAR^{high}$) (B) and the breast cancer cell lines BT-20 ($αvβ6^{high}$/$hCAR^{neg}$) and MDA-MB-231 ($αvβ6^{neg}$/$hCAR^{high}$) (C) were plated in a 96 well plate at a density of 20,000 cells/well. Cells were infected with 5,000 vp/cell, and cell viability was quantified every 24 hours using a standard MTS cell viability assay. As expected, replication deficient vectors did not exhibit detrimental effects on cell viability, whilst the cell killing (oncolytic) activity of OAd5.3D.A20 and OAd5 was directly related to the presence/absence of cellular αvβ6 and hCAR.

DETAILED DESCRIPTION

Materials and Methods
Adenovirus Vectors, Cell Lines and Clinical Ascites

All generated vectors were luciferase (Luc)-expressing and based on a wild type Ad5 genome captured in a bacterial artificial chromosome (BAC). All genetic modifications were introduced into the BACs by AdZ homologous recombineering methods (Stanton et al., 2008) as described previously (Uusi-Kerttula et al., 2016). Viruses were produced in T-Rex 293 or HEK293-β6 cells (A20-modified viruses). Replication-deficient vectors carry a complete E1/E3 gene deletion, whilst oncolytic vectors have a 24-base pair deletion d1922-947 (Δ24) (Fueyo et al., 2000) in the E1A gene to restrict viral replication to pRB-defective cells (Sherr, 1996), and T1 mutation, a single adenine base addition at position 445 within the endoplasmic reticulum (ER) retention domain in E3/19K for enhanced oncolytic potency (Gros et al., 2008). Heterologous A20 peptide sequence (NAVPNLRGDLQVLAQKVART; SEQ ID NO: 1) from FMDV was genetically inserted into the fiber knob HI loop. High titre viruses were produced in T-REx-293 or HEK293-β6 cells, essentially as described previously (Uusi-Kerttula et al., 2015, Uusi-Kerttula et al., 2016).

SKOV3-β6 cell line was generated in-house. Puromycin-selective pBABE-β6 plasmid with 66 gene insertion (#13596; Addgene) was transfected into a 293Phoenix packaging cell line using Effectene. After 48 h, retrovirus was harvested and filtered, and used to infect SKOV3 cells; αvβ6 integrin-expressing cells were selected in the presence of 5 µg/mL puromycin. Permission for the collection and cultivation of primary EOC cells from ascites was granted through a Wales Cancer Bank application for biomaterials, reference WCB 14/004. All patients gave written informed consent prior to collection. Ascites clinical samples were collected from patients undergoing treatment for advanced ovarian cancer at Velindre Cancer Centre, Cardiff and anonymised. Cells were processed and sub-cultured as described previously (Uusi-Kerttula et al., 2015, Uusi-Kerttula et al., 2016).

In Vitro Assays

Cell surface receptor expression was assessed by flow cytometry as described previously (Uusi-Kerttula et al., 2016), using an anti-αvβ6 clone 10D5 and an anti-CAR antibody clone RmcB, followed by a secondary F(ab')2-goat α-mouse IgG (H+L) IgG AlexaFluor647. The presence of anti Ad5 antibodies in ovarian ascites and serum was determined essentially according to a previously reported ELISA method (Stallwood et al., 2000). Antigen specificity of the antibodies was assessed by Western blot.

Cell transduction efficiency in vitro was assessed in luciferase reporter gene assays essentially as described earlier (Uusi-Kerttula et al., 2015, Uusi-Kerttula et al., 2016) on a multimode plate reader, and relative light units (RLU) normalised to total protein concentration in each well (RLU/mg). To assess the effect of FX on transduction efficiency, transduction media were supplemented with 10 µg/mL of human FX. Vector tropism for cellular receptors was assessed in competition inhibition assays as described previously (Uusi-Kerttula et al., 2016), using anti-αvβ6 antibody (10 µg/mL; clone 10D5, Millipore) or normal antimouse control IgG (10 µg/mL; Santa Cruz). Neutralisation assays involved a pre-incubation step in 2-fold serial dilutions (1:40-1:2.5, corresponding to final concentration of 2.5-40%) of cell-free OAS.

In Vivo Studies

All animal experiments were performed at Mayo Clinic, Rochester, USA. For consistency of results, all animals were 7 weeks old and sex-matched; female mice were chosen due to the ease of housing. All animal handling and injections were performed by an experienced veterinary technologist Mrs Jill M. Thompson as per local regulations.

Biodistribution study on replication-deficient vectors was performed in wild type B6 albino mice (B6N-Tyr$^{c-Brd}$/BrdCrCrl) (n=5/group) due to the feasibility of its white coat for luciferase tracking. Viruses were injected into the lateral tail vein at $1×10^{11}$ vp. All mice were sacrificed after IVIS imaging at 72 h post-infection by inhalation of $CO_2$, and organs harvested for analysis. Efficacy study was performed in immunocompromised NOD/SCID mice (n=5/group). Treatment schedule was first optimised in a pilot study (n=8). $1×10^7$ SKOV3-β6 cells were implanted i.p. on day 0, and two mice sacrificed on days 7, 14, 21 and 48/49 (final endpoint). CAR and αvβ6 expression in tumours at each time point was assessed by flow cytometry. In the oncolytic efficacy study, NOD/SCID mice were xenografted i.p. with $1×10^7$ of SKOV3 or SKOV3-β6 cells on day 0. Mice (n=5/group) were then treated with an i.p. injection of $1×10^{10}$ vp of OAds (PBS, OAd5 and OAd5.3D.A20) on days 14, 16 and 18. The primary endpoint was overall survival (%). Vector uptake was monitored by quantifying the luminescence signal emitted by the luciferase transgene in Xenogen IVIS 200 imager (PerkinElmer). Viral genome copy number in primary off-target organs and endpoint tumours was quantified by qPCR. The level of αvβ6 gene expression in endpoint tumours was quantified by qPCR.

Cell Viability Assay Brief Protocol

For cell viability assays, the CellTiter 96 AQueous One Solution Cell Proliferation assay (Promega) was used according to the manufacturer's recommended protocol. 20,000 or 30,000 cells were seeded into each well of a 96 well plate and incubated overnight. Cells were infected with 5,000 viral particles per cell (vp/cell) for 3 hours in serum free media. Viable cells were determined at 24, 48, 72, 96 and 144 hours after infection, by adding 20 µl CellTiter 96 AQueous One Solution reagent per well. Absorbance was measured at 490 nm after 2 hours incubation in a humidified 5% CO2 atmosphere. % viable cells were calculated related to untreated cells. Results are mean, n=3, error bars represent standard deviation.

Statistical Analyses

All figures and statistical analyses were done in GraphPad Prism version 6.03. In vitro and ex vivo assays were analysed by two-tailed unpaired t-tests or one-way ANOVA with Dunnett's multiple comparisons post hoc test. In vivo data was normalised and analysed by one-way ANOVA with Sidak's multiple comparisons post hoc test. Overall survival (%) following oncolytic treatment is shown as a Kaplan-Meier survival curve; survival proportions were analysed by Gehan-Breslow-Wilcoxon test. All tests: ns, $p>0.05$; *, $p<0.05$; , $p<0.01$; * $p<0.001$; **** $p<0.0001$.

Results

We generated and produced high viral titres replication-defective and oncolytic variants of a novel Ad5.3D.A20 vector with three de-targeting mutations and an A20 peptide insertion that re-targets the vector to $\alpha v\beta 6$ integrin-expressing cells (FIG. 1). The multiple genetic manipulations did not have a significant impact on titre. Predictive modelling in SWISS147 MODEL platform indicated a protrusion of the A20 peptide within the immunodominant HI loop (FIG. 1C).

Figure 2B:
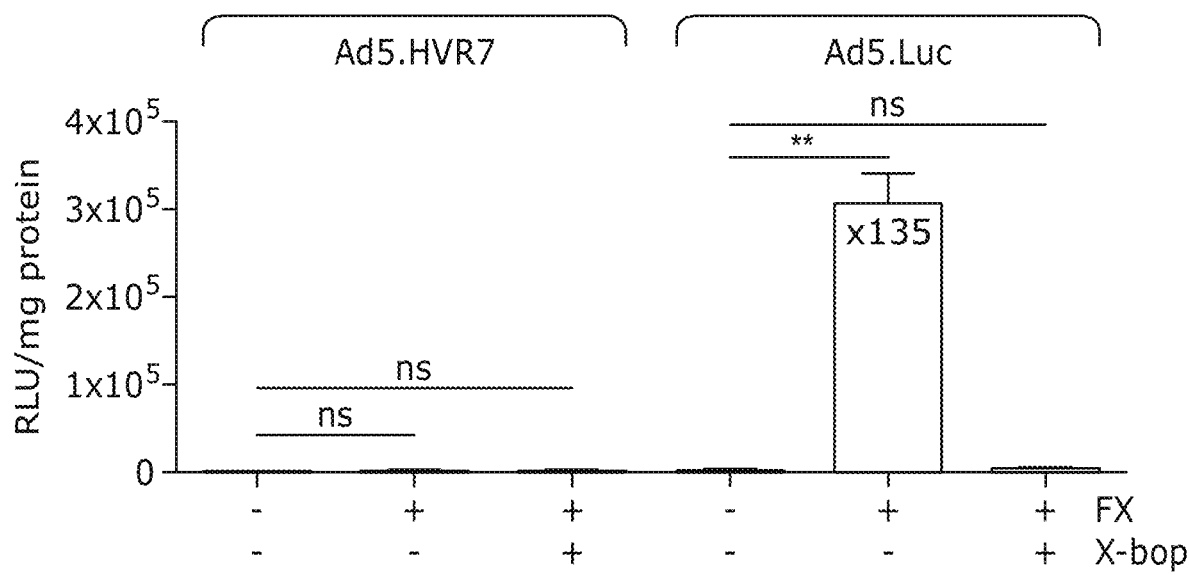
Figure 3A:
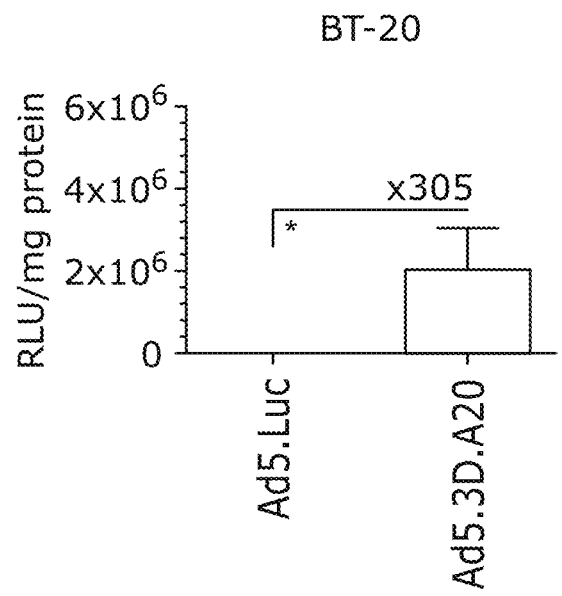
Figure 3B:
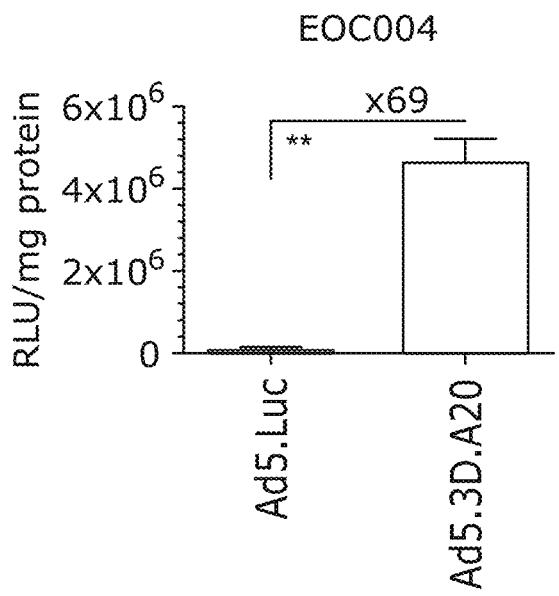
Figure 3C:
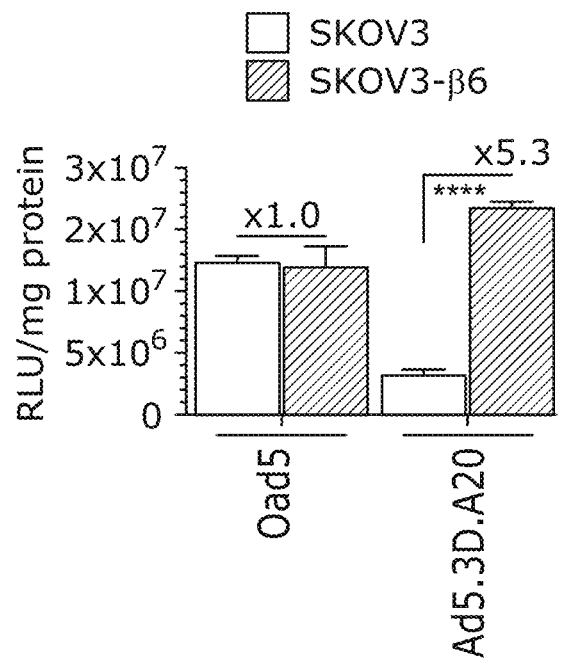
Figure 3D:
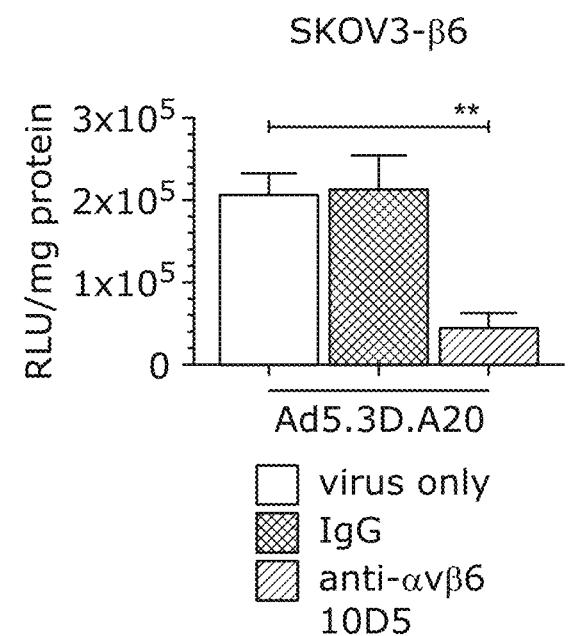

The transduction efficiency of replication-deficient vectors was assessed in cell lines expressing variable amounts of CAR and $\alpha v\beta 6$ integrin. The de-targeting mutations of Ad5.3D.A20 completely abolished entry via CAR in CHO-CAR cells (CAR+), while Ad5 transduced these cells efficiently (FIG. 2A). The HVR7 mutation abolished vector transduction via FX (FIG. 2B). As expected, FX significantly increased transduction of Ad5 into these cells as compared to FX-free culture conditions (FIG. 2B; right panel). Conversely, addition of human FX in culture medium had no effect on the transduction efficiency of the FX binding ablated Ad5.HVR7 control vector in CHO-K1 cells (FIG. 2B; left panel). Furthermore, the enhanced transduction seen for Ad5 was reversed by the addition of a 3:1 molar excess of Gla-domain interacting protein, anticoagulant X-bp, that binds to and inactivates FX in the medium (FIG. 2B, right panel). On the contrary, FX depletion did not affect the transduction of Ad5.HVR7 vector (FIG. 2B, left panel).

$\alpha v\beta 6$ integrin has been confirmed as the primary entry receptor for triply de-targeted, integrin re-targeted Ad5.3D.A20 (FIG. 3). Ad5.3D.A20 transduced $\alpha v\beta 6+/$CAR− BT-20 breast cancer cells with 305-fold higher efficiency (FIG. 3A; p=0.0270) and primary EOC004 cells ($\alpha v\beta 6+/$CAR−) at 69-fold increased efficiency (FIG. 3B; p=0.0090) relative to Ad5. Additionally, an oncolytic variant of the Ad5.3D.A20 vector transduced SKOV3-$\beta 6$ cells ($\alpha v\beta 6$-high/CAR+) at ~5-fold increased efficiency relative to SKOV3 cells that express low levels of $\alpha v\beta 6$ ($\alpha v\beta 6$-low/CAR+, FIG. 3C; p<0.0001), confirming that oncolytic modifications had not compromised A20 peptide:$\alpha v\beta 6$ interaction. Competition assays using an anti-$\alpha v\beta 6$ antibody (10D5) significantly inhibited transduction by Ad5.3D.A20 vector (169 FIG. 3D; p=0.0010), confirming selectivity for $\alpha v\beta 6$.

Figure 4A:
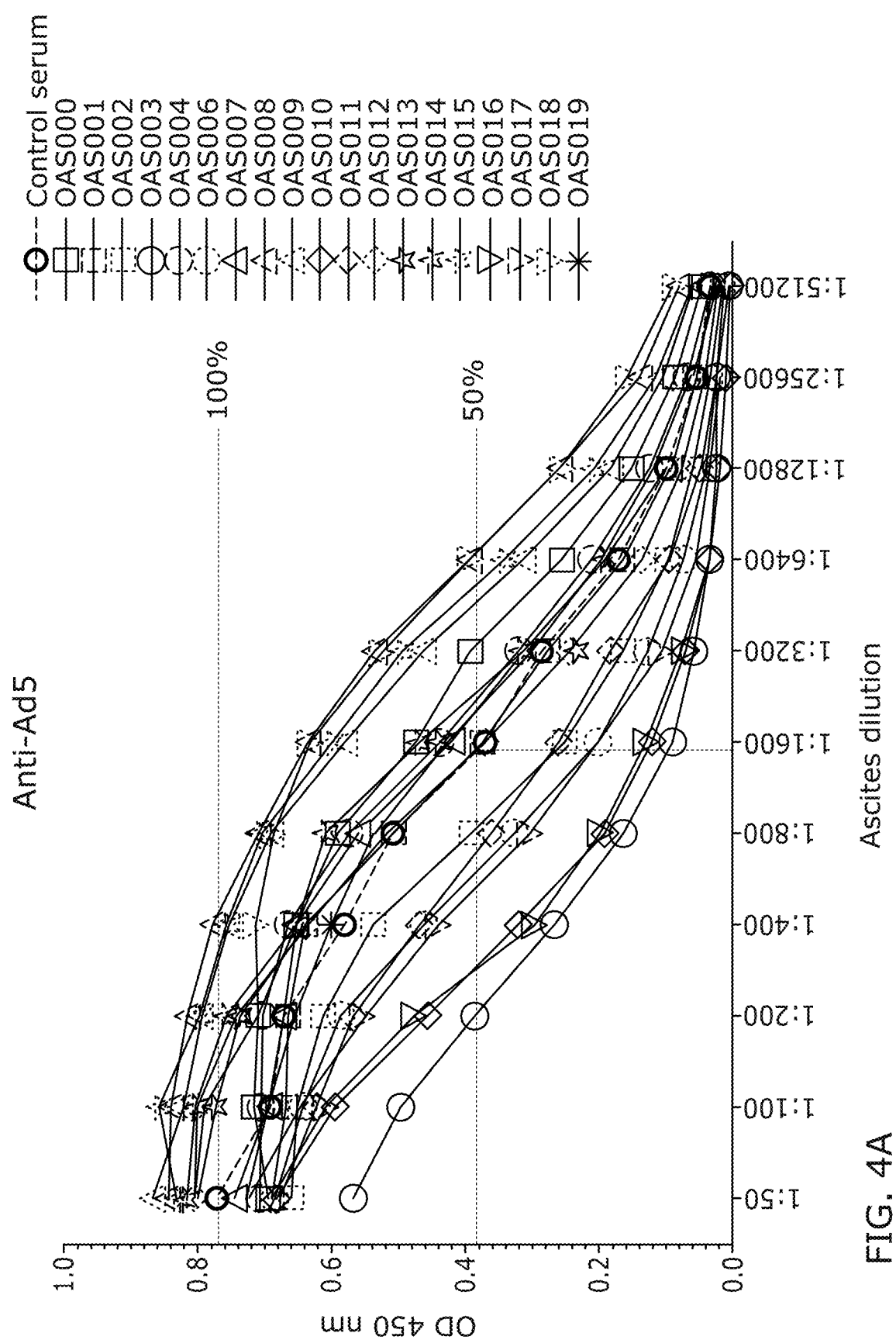
Figure 4B:
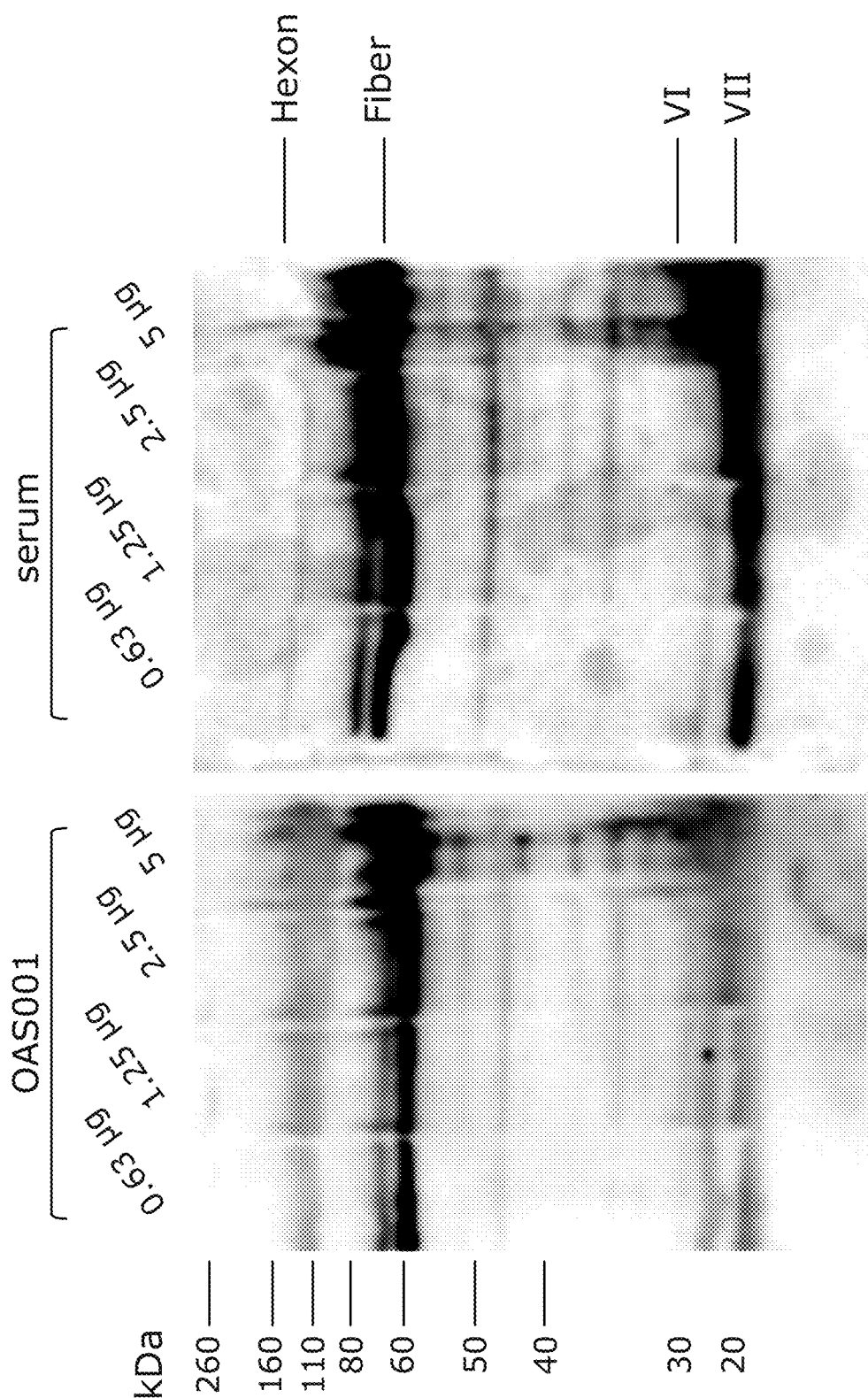
Figure 4C:
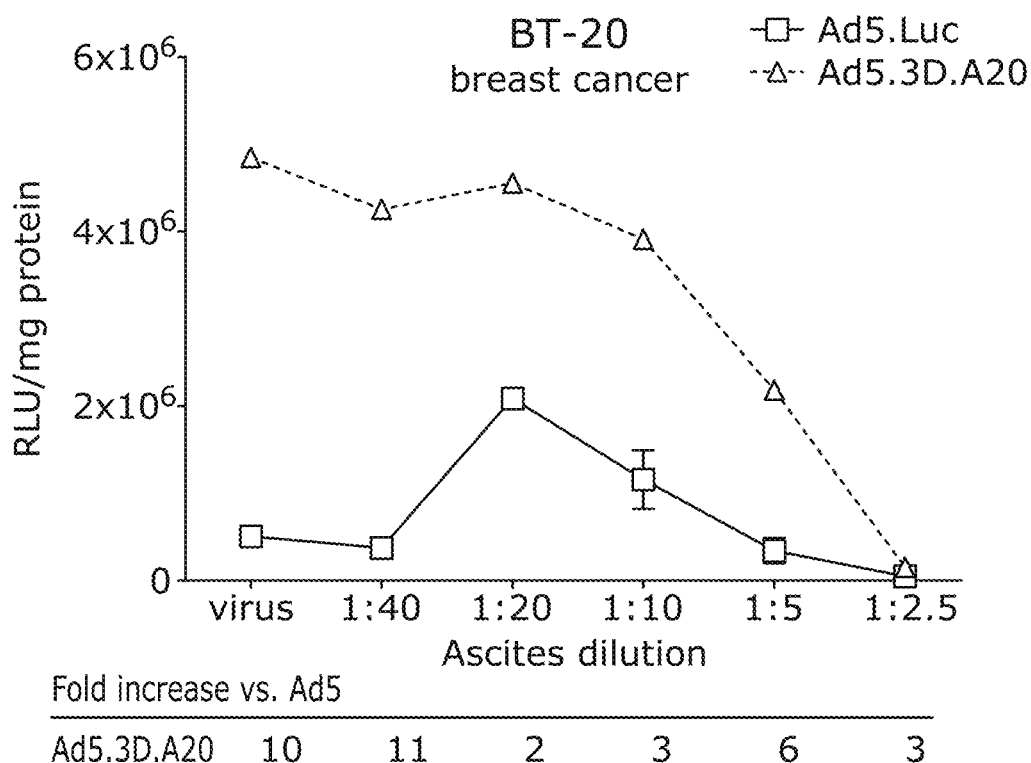
Figure 4D:
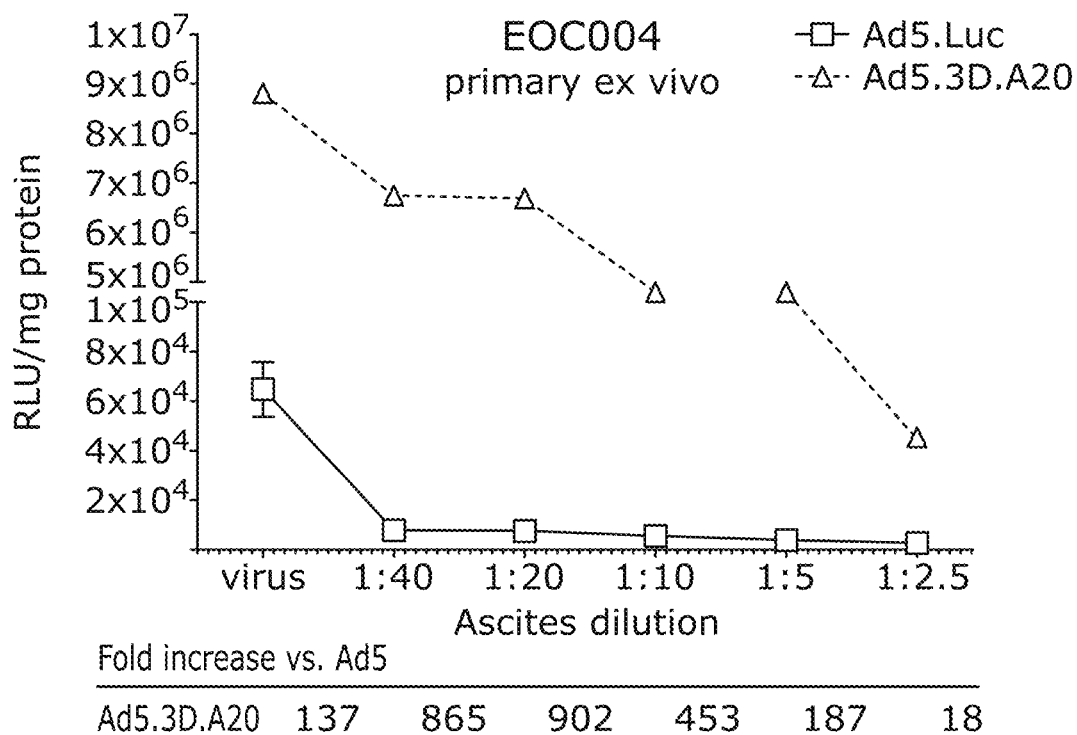

Clinical ovarian ascites (OAS) samples from twenty patients were screened for the presence of anti-Ad5 antibodies by ELISA. The titres of anti-Ad5 abs in malignant ovarian ascites were scrutinised against the serum anti-Ad5 antibody titre of a healthy adult male volunteer (FIG. 4A). Equal proportion of patients were found to have lower and higher antibody titres than the control serum (FIG. 4A, black dashed line). Ascites from patient 001 (OAS001) was chosen for subsequent neutralisation assays due to its similar antibody titre with the control serum. Antibodies in OAS001 and control serum appeared specific for the fiber protein, whilst the most abundant capsid protein hexon was recognised only at very low levels in Western blot using denatured viral particles (FIG. 4B). The neutralising effect of OAS001 on transduction efficiency of Ad5.3D.A20 was assessed in $\alpha v\beta 6+/$CAR− EOC004 primary cells. Ad5.3D.A20 showed superior transduction efficiency (up to 902-fold higher) relative to Ad5 at OAS concentrations of 2.5, 5 and 10%, while Ad5 did not transduce these cells at detectable levels (FIG. 4C).

Figure 5A:
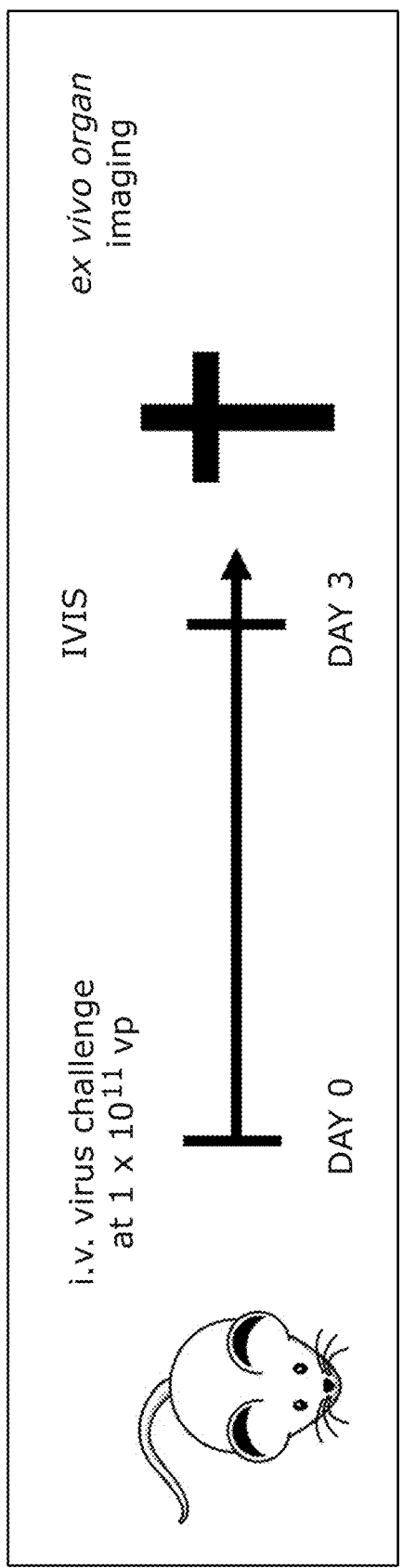
Figure 5B:
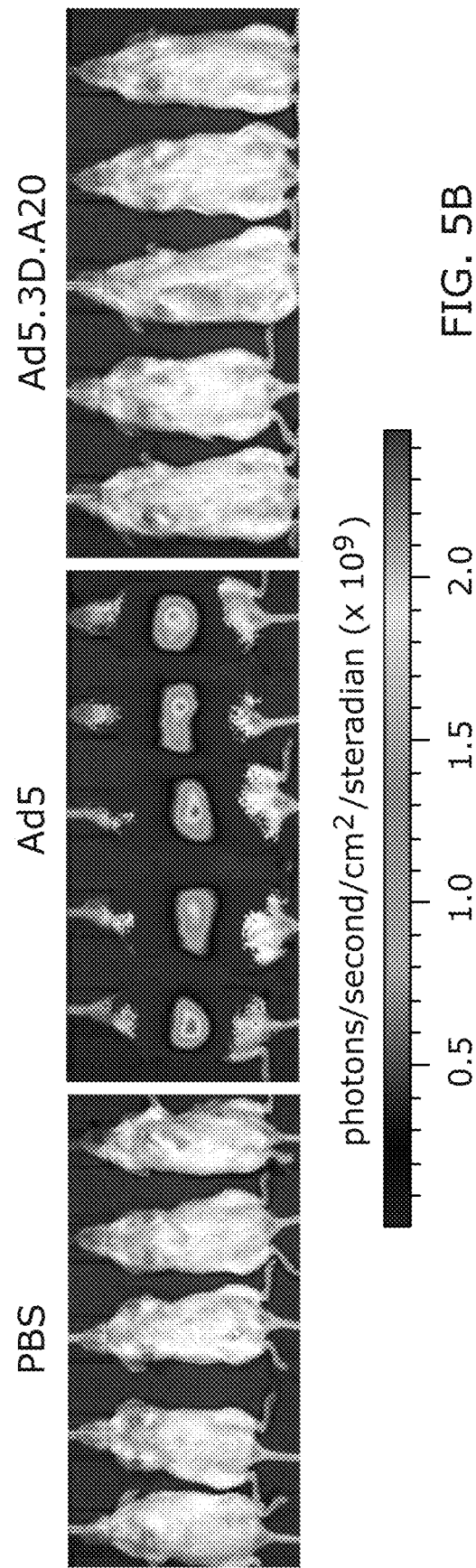
Figure 5C:
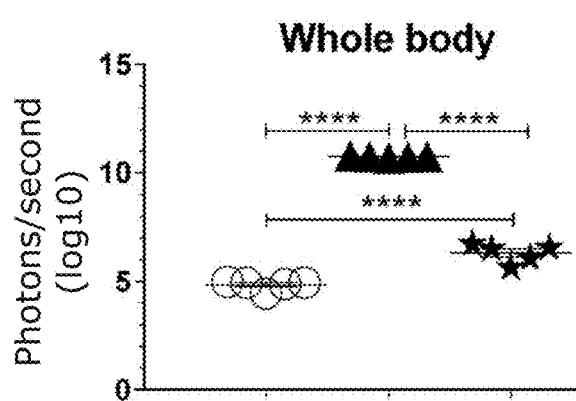
Figure 5D:
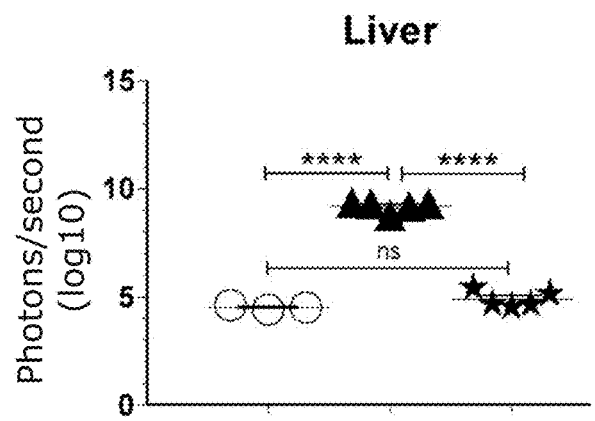
Figure 5E:
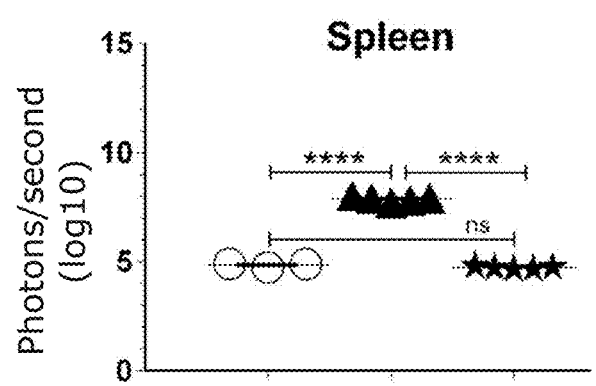
Figure 5F:
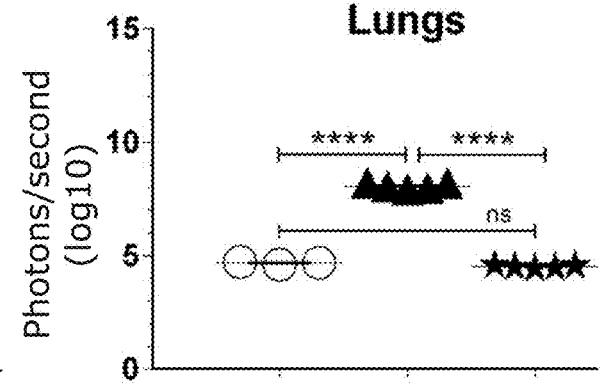
Figure 5G:
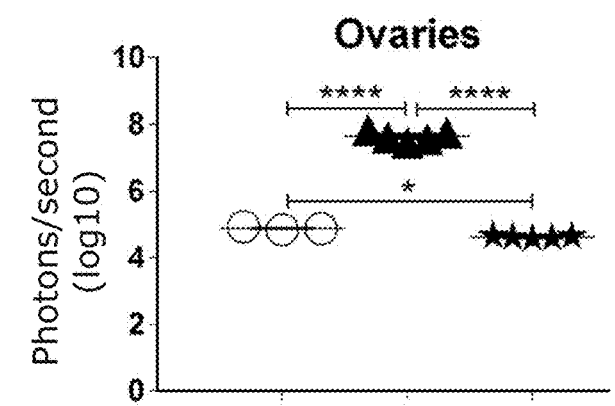
Figure 5H:
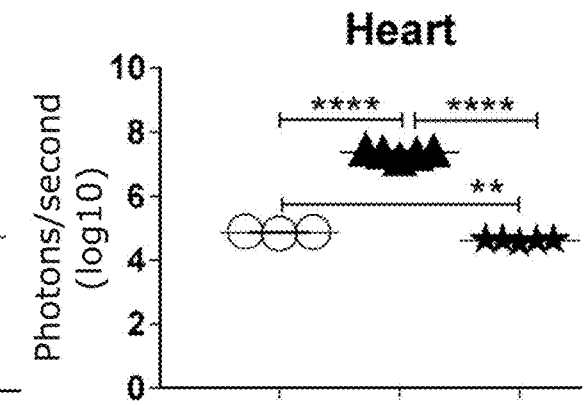

Non-tumour-bearing mice were inoculated intravenously to assess vector tropism in vivo, in particular the effect of the three de-targeting mutations on vector biodistribution (FIG. 5A). Ad5 showed intense localisation in the area of liver and spleen, while luminescence by the Ad5.3D.A20 vector was undetectable at 72 h (FIG. 5B). Animals inoculated with Ad5 had significantly higher whole body luminescence than control animals treated with PBS (p<0.0001) or Ad5.3D.A20 (p<0.0001) (FIG. 5C). The liver, spleen, lungs, ovaries and heart were removed and quantified for ex vivo luminescence (for luminescence heat-maps, see FIG. 8A-C). The livers of Ad5-challenged animals emitted significantly more luminescence than the PBS control or Ad5.3D.A20 groups (both p<0.0001) (FIG. 5D). Similarly, Ad5.3D.A20 had significantly decreased transgene expression in the spleen, lungs, ovaries and heart, relative to Ad5 (FIG. 5E-H; p<0.0001 for all). For fold changes in luminescence intensity in each organ, see FIG. 8D.

Figure 9A:
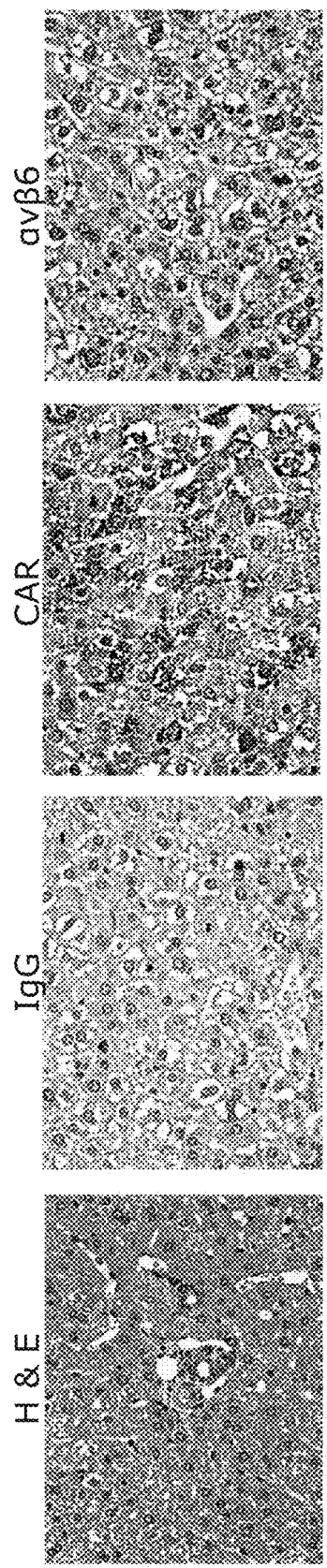
Figure 9B:
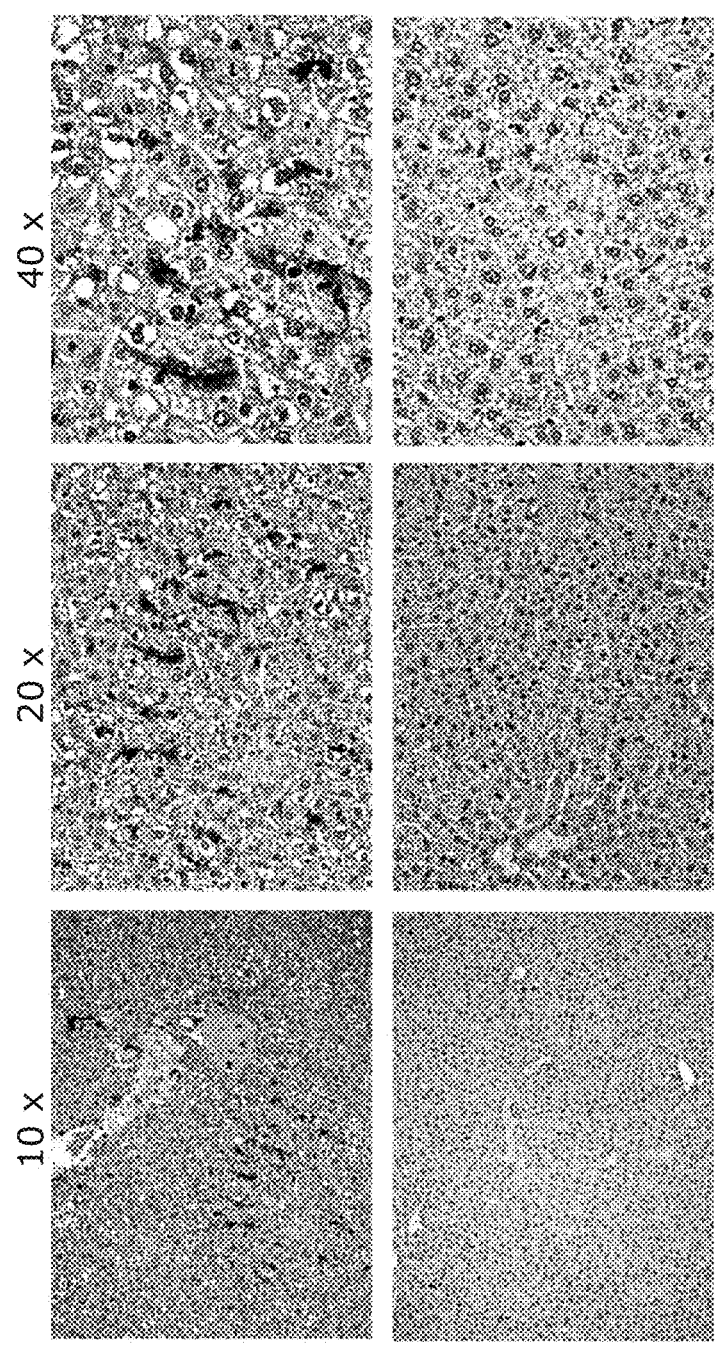

Confirmation that the modifications in Ad5.3D.A20 resulted in 196 reduced sequestration of virus in multiple normal tissues was confirmed via quantitation of viral load in off-target organs by qPCR. Genome copy number of Ad5.3D.A20 was 10 million times lower in the liver relative to the Ad5 (FIG. 6A; p<0.0001). Similarly, Ad5.3D.A20 genome copy number was more than 700-fold lower in the spleen compared to Ad5 (FIG. 6B; p<0.0001). In addition, the Ad5.3D.A20 vector showed improved off-target profiles in all organs relative to Ad5, with viral load 105, 104 and 103 lower in the lungs, heart and ovaries, respectively (FIG. 6C-E). Successful de-targeting of the liver being due to our genetic modifications of Ad5 is supported by immunohistochemical staining of liver sections, which showed high expression levels of CAR, whilst $\alpha v\beta 6$ was undetectable (FIG. 9A). Confirmation of the de-targeting effects of genetic modifications in Ad5.3D.A20 is provided by the observation that liver sections from mice showed positive staining for Ad capsid proteins in the Ad5 group, but not in livers of mice that had been challenged with the Ad5.3D.A20 vector (FIG. 9B).

To evaluate efficacy of $\alpha v\beta 6$ re-targeting in an in vivo cancer model, $\alpha v\beta 6$-high/CAR-SKOV3-$\beta 6$ human ovarian cancer xenografts were established in immuno-compromised NOD/SCID mice. Animals developed large solid tumours at the cell injection site and at various sites within the peritoneal cavity within 14 days after intra-peritoneal implantation of SKOV3-$\beta 6$ cells and by day 49, tumours were spread throughout the peritoneal cavity with accumulation of large volumes of ascites. Tumours retained high $\alpha v\beta 6$ expression (for flow cytometry, see FIG. 10). Based on these observations, we performed virotherapy efficacy studies by delivering three intravenous doses of oncolytic variants of Ad5 and Ad5.3D.A20 on days 14, 16 and 18 post-implantation of αvβ6-low/CAR- SKOV3 and αvβ6-high/CAR- SKOV3-β6.

Figure 7C:
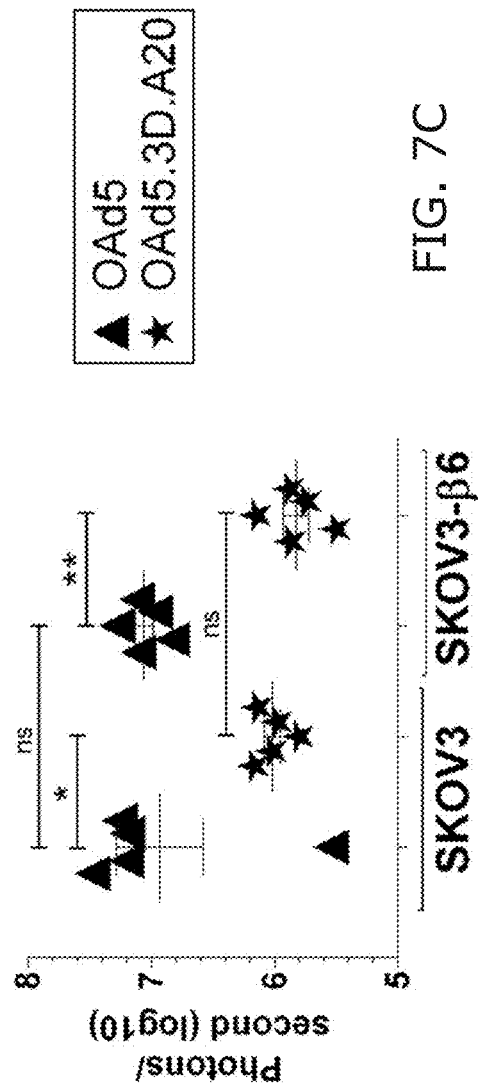
Figure 7D:
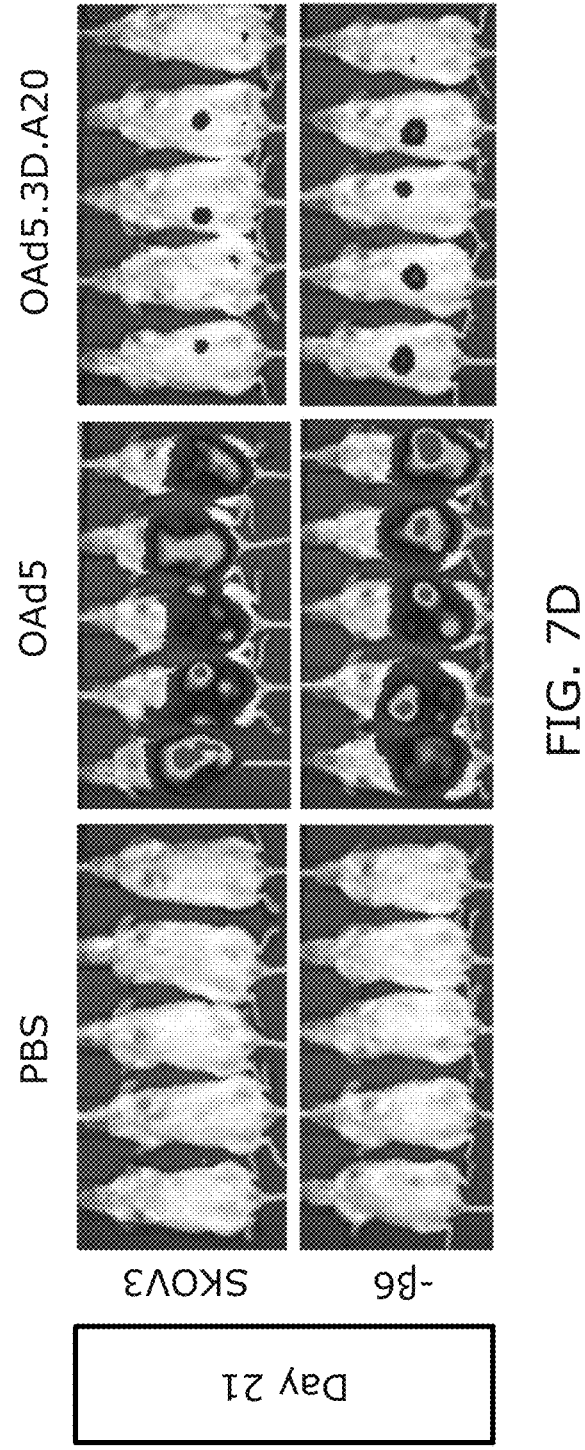
Figure 7E:
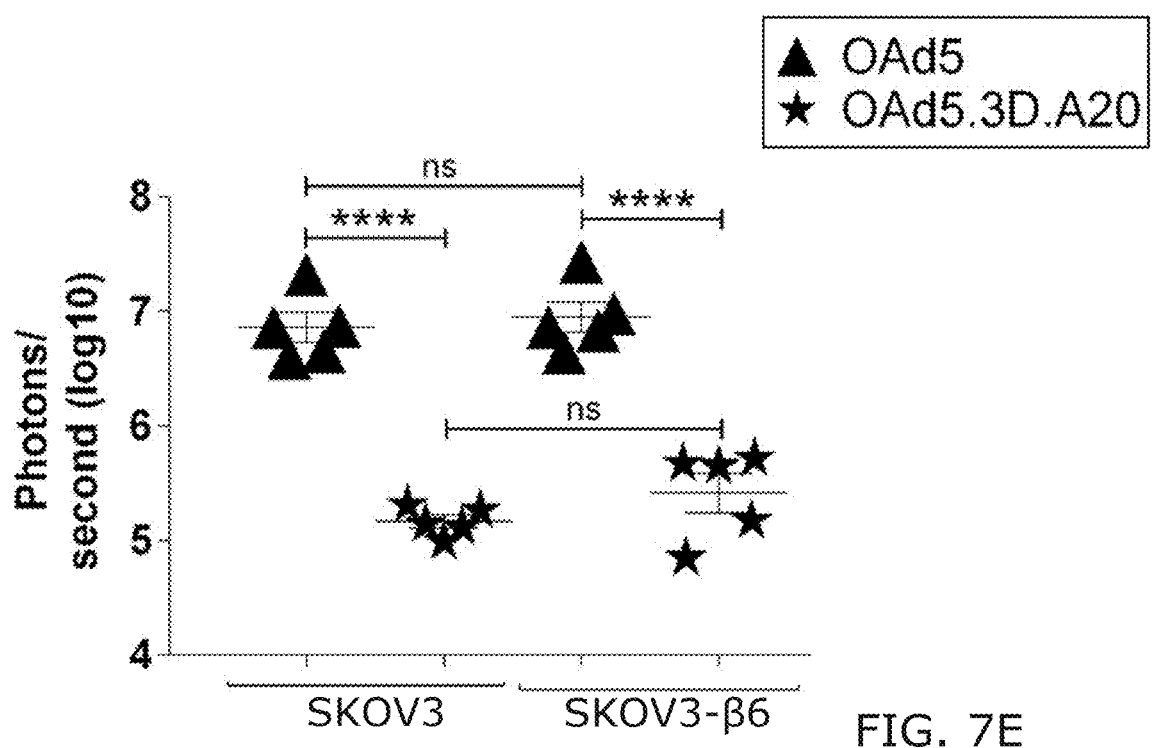

IVIS imaging at 48 h after first virotherapy treatment dose (day 16) showed widespread luminescence throughout the abdominal region in animals treated with the oncolytic Ad5 vector, with highest intensity in the liver/spleen region, in both SKOV3 and SKOV3-β6 xenograft models (FIG. 7B). This distribution was maintained, but at lower intensity, 5 days later, on day 21 (FIG. 7D). In contrast, the Ad5.3D.A20 223 vector however, showed very selective localisation, with significantly reduced overall luminescence relative to Ad5, consistent with successful de-targeting of non-tumour tissues. For both SKOV3 and SKOV3-β6 models, quantitation of total body luminescence showed uptake of the Ad5.3D.A20 vector to be significantly lower than Ad5 both on day 16 (FIG. 7C; p<0.05 and <0.01, respectively) and on day 21 (FIG. 7E; p<0.0001).

Figure 7F:
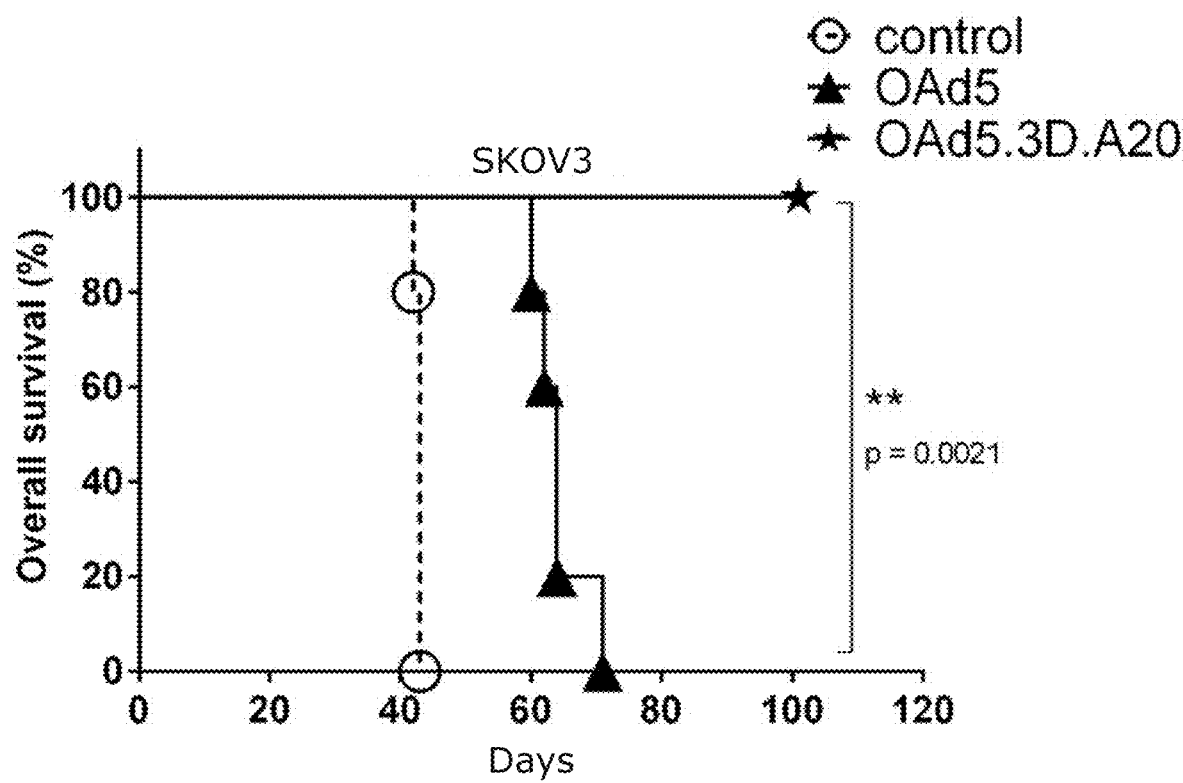

Anti-tumour activity was seen for both oncolytic Ad5 and oncolytic Ad5.3D.A20 in the SKOV3 xenograft model (FIG. 7F). Consistent with an enhanced tumour-selective effect of Ad5.3D.A20, all five mice treated with Ad5.3D.A20 were still alive at the final time point of 101 days, while animals treated with Ad5 only survived for up to 70 days.

Figure 14A:
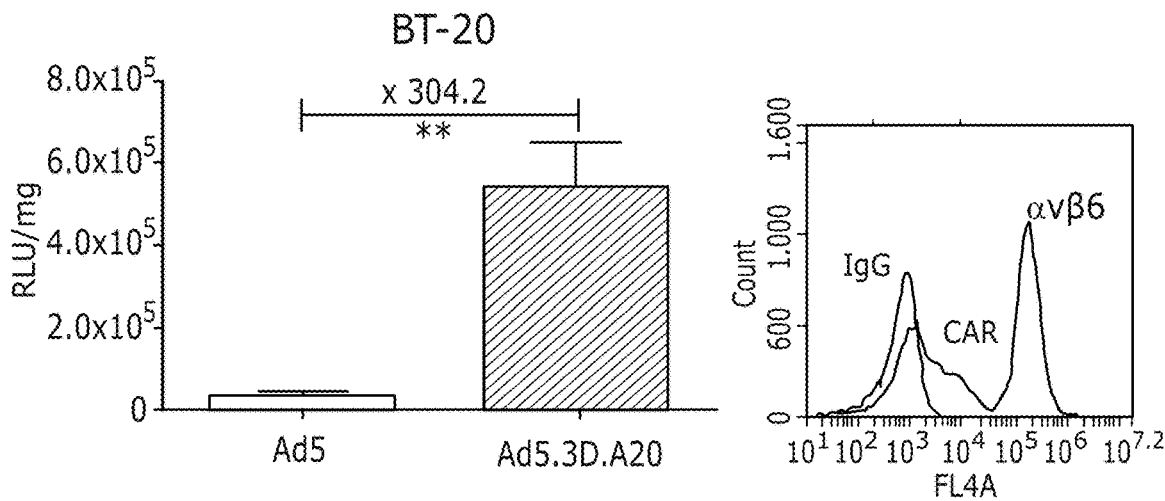
Figure 14B:
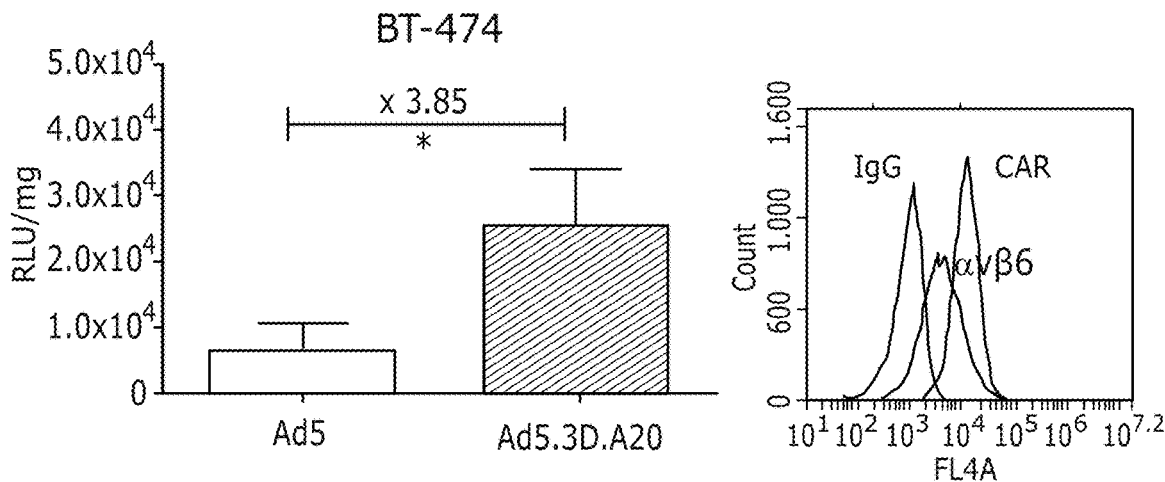
Figure 14C:
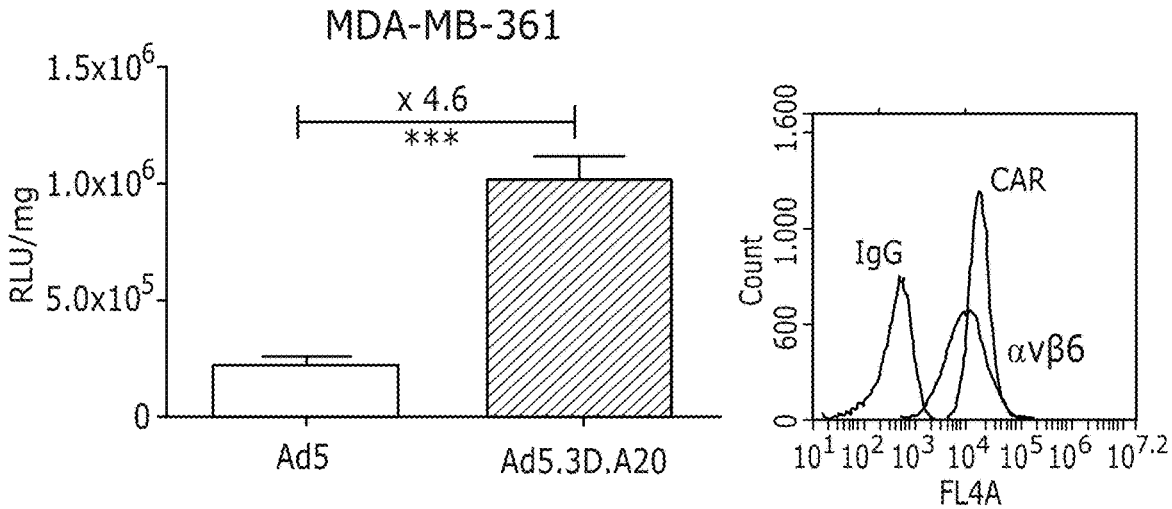
Figure 14D:
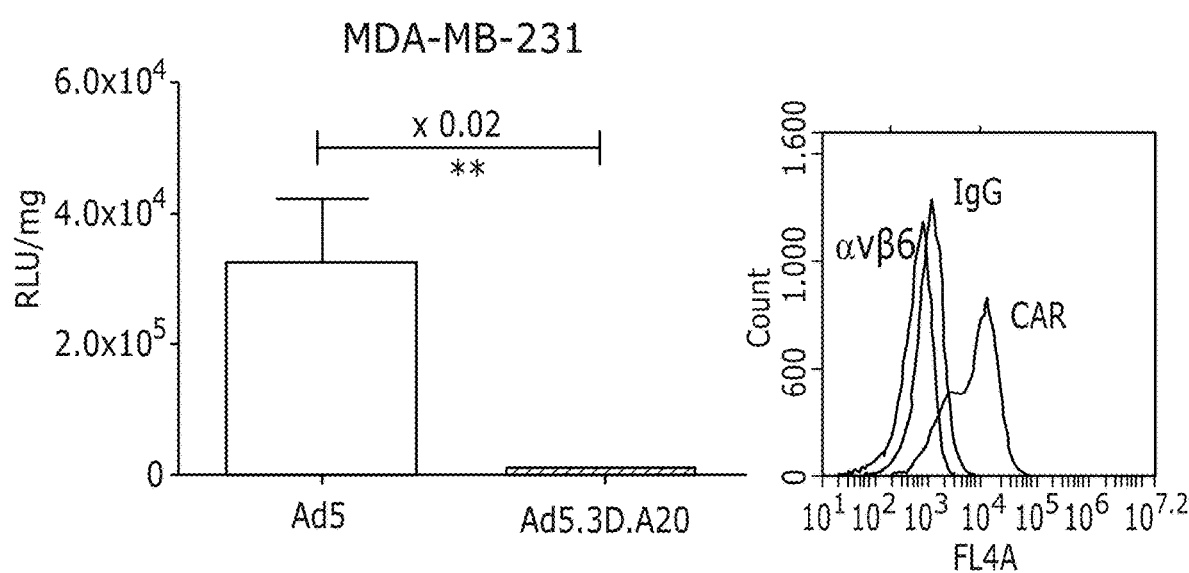

We performed additional transduction assays in a range of cancer cell lines of pancreatic (FIG. 12), oesophageal (FIG. 13), breast (FIG. 14) and lung (FIG. 15) origin. All cell types were first analysed for αvβ6 and hCAR expression (histograms in each figures). 7/9 pancreatic cell lines (ASPC-1, BxPc, CFPAC, PANC 10.05, SW1990, PANC 0403 and Suit2 expressed αvβ6 to varying levels and could be efficiently transduced with Ad5.3D.A20 (FIG. 12A-G). Conversely, MiPaCa2 (FIG. 12H) and PT45 (FIG. 12I) cells expressed very low or no αvβ6 and were poorly permissive to Ad5.3D.A20 mediated transduction, as would be predicted. The oesophageal cell lines Kyse-30 expressed high levels of αvβ6 and was highly permissive to Ad5.3D.A20 mediated transduction (FIG. 13). In breast cancer cell lines tested 3 of 4 cell lines tested (BT-20, BT-474 and MDA-MB361) expressed αvβ6 to varying extents and were permissive to transduction by Ad5.3D.A20 (FIG. 14A-C), whilst conversely the lack of expression of αvβ6 in MDA-MB-231 cells rendered the cells non-infectious to Ad5.3D.A20 (FIG. 14D). In all 3 lung cancer cell lines tested (A427, A549 and NCI-H460, FIG. 15A-C), αvβ6 was absent and the cells were refractive to Ad5.3D.A20 mediated transduction.

To evaluate cell killing activity of oncolytic versions of Ad5.3D.A20, cell viability assays were performed in αvβ6$^{high}$ (Suit2, Panc0403) and αvβ6$^{low}$ (MiPaCa2) or αvβ6$^{neg}$ (PT45) pancreatic cancer cell lines (FIG. 16). Cells were infected with 5,000 vp/cell of either replication deficient Ad5 or Ad5.3D.A20 or oncolytic (O) Ad5 or Ad5.3D.A20. As expected, replication deficient vectors did not mediate any significant effects on cell viability, whilst cell killing activity of the oncolytic vectors was shown to correlate well with αvβ6 expression. Similarly, in the αvβ6$^{high}$/hCAR$^{neg}$ triple negative breast cancer cell line BT-20, the presence of high levels of αvβ6 coupled with the lack of hCAR resulted only OAd5.3D.A20 being able to efficiently mediate cell killing. Conversely in the αvβ6$^{neg}$/hCAR$^{high}$ breast cancer cell line MDA-MB-231, only OAd5 could efficiently kill cells due to the presence of hCAR and absence of αvβ6.

DISCUSSION

We describe a novel, tumour-selective oncolytic adenoviral vector, Ad5.3D.A20 which is ablated for all known native tropisms and re-targeted to an over-expressed, prognostic cancer marker—αvβ6 integrin. Integrin αvβ6 is a promising target for therapeutic cancer applications due to its expression in aggressively transformed cancers.

In the present study, a replication-defective form of Ad5.3D.A20 vector successfully de-targeted viral uptake by cells via native viral uptake pathways (FIG. 2), instead selectively re-targeting αvβ6+ cells, in vitro and ex vivo (FIG. 3). Although the efficacy-limiting interactions that occur in systemic delivery of adenoviral vectors can, theoretically, be by-passed by intra cavity administration of the vector, via the i.p. route, in practice this approach presents challenges since wild-type Ad5 is sequestered by anti-Ad5 nAbs in ascitic fluid. We therefore assessed the transduction efficiency of Ad5.3D.A20 in the presence of OAS with high pre-existing levels of anti-Ad5 nAbs (FIG. 4A). Unlike Ad5, Ad5.3D.A20 retained its ability to transduce αvβ6+ cells, even at relatively high OAS concentrations (FIG. 4C).

Clinical efficacy of Ad5 vectors with unmodified capsids is also significantly limited by off-target tissue sequestration, particularly in the liver. We demonstrate that Ad5.3D.A20 successfully altered the biodistribution of the Ad5 vector in vivo. In tumour-free mice, replication-deficient Ad5.3D.A20 demonstrates improved biodistribution compared to the parental Ad5, with significantly reduced viral transgene expression the liver, spleen and lungs (FIG. 5), and lower viral genome copy number in all off-target organs 274 compared to Ad5 (FIG. 6).

To test efficacy of an oncolytic form of our de-targeted/re-targeted Ad5.3D.A20 vector, we established an orthotopic i.p. xenograft model of human ovarian cancer in immunocompromised mice. The more localised bio-distribution of virally-encoded transgene expression of oncolytic Ad5.3D.A20 following intraperitoneal administration was consistent with reduced off-target sequestration and/or tumour-selective virus uptake (FIG. 7B-E). This was supported by the superior survival of animals treated with Ad5.3D.A20 relative to Ad5, in a SKOV3 xenograft model (FIG. 7F).

Ad5.3D or Ad5.3D.A20 administration presents a promising treatment option for advanced, chemotherapy-resistant cancer or αvβ6+ cancer, particularly but not exclusively ovarian cancer, pancreatic cancer, oesophageal cancer and breast cancer, respectively. This vector provides an important platform that could ultimately be modified for precision viral therapy applications.

REFERENCES

FUEYO, J., GOMEZ-MANZANO, C., ALEMANY, R., LEE, P. S. Y., MCDONNELL, T. J., MITLIANGA, P., SHI, Y. X., LEVIN, V. A., YUNG, W. K. A. & KYRITSIS, A. P. 2000. A mutant oncolytic adenovirus targeting the Rb pathway produces anti-glioma effect in vivo. Oncogene, 19, 2-12.

GROS, A., MARTINEZ-QUINTANILLA, J., PUIG, C., GUEDAN, S., MOLLEVI, D. G., ALEMANY, R. & CASCALLO, M. 2008. Bioselection of a gain of function mutation that enhances adenovirus 5 release and improves its antitumoral potency. Cancer Research, 68, 8928-8937.

SHERR, C. J. 1996. Cancer cell cycles. Science, 274, 1672-1674.

STALLWOOD, Y., FISHER, K. D., GALLIMORE, P. H. & MAUTNER, V. 2000. Neutralisation of adenovirus infectivity by ascitic fluid from ovarian cancer patients. Gene Therapy, 7, 637-643.

STANTON, R. J., MCSHARRY, B. P., ARMSTRONG, M., TOMASEC, P. & WILKINSON, G. W. G. 2008. Re-engineering adenovirus vector systems to enable high-throughput analyses of gene function. BioTechniques, 45, 659-668.

UUSI-KERTTULA, H., DAVIES, J., COUGHLAN, L., HULIN-CURTIS, S., JONES, R., HANNA, L., CHESTER, J. D. & PARKER, A. L. 2016. Pseudotyped alphavbeta6 integrin-targeted adenovirus vectors for ovarian cancer therapies. Oncotarget.

UUSI-KERTTULA, H., LEGUT, M., DAVIES, J., JONES, R., HUDSON, E., HANNA, L., STANTON, R. J., CHESTER, J. D. & PARKER, A. L. 2015. Incorporation of Peptides Targeting EGFR and FGFR1 into the Adenoviral Fiber Knob Domain and Their Evaluation as Targeted Cancer Therapies. Hum Gene Ther, 26, 320-9.

(iii) an insertion of a peptide comprising a YSA motif in the chimeric fiber.

7. The adenovirus according to claim 6 wherein the tumor-cell targeting mutation comprises the A20 peptide insertion.

8. The adenovirus according to claim 7 wherein the A20 peptide has a sequence comprising NAVPNLRGDLQVLAQKVART (SEQ ID NO: 1).

9. The adenovirus according to claim 8 further comprising a transgene encoding a therapeutic molecule or agent.

10. The adenovirus according to claim 7 further comprising a transgene encoding a therapeutic molecule or agent.

11. The adenovirus according to claim 6 further comprising a transgene encoding a therapeutic molecule or agent.

12. The adenovirus according to claim 6 further comprising a 24-base pair deletion d1922-947 in the E1A gene.

The invention claimed is:

1. A viable modified Ad5 serotype adenovirus having mutations comprising a) I421G, T423N, E424S, E450Q and L426Y mutations in the hexon hypervariable region 7 (HVR7 mutation);

b) S408E and P409A mutations in the fiber knob region AB loop (KO1 mutation);

c) D342E mutation in the penton integrin binding motif Arg-Gly-Asp (RGD mutation); and d) a tumor-cell targeting mutation;

whereby:

the HVR7 mutation, KO1 mutation, and RGD mutation prevent virus binding with FX, CAR, and $\alpha v\beta_3/\alpha v\beta_5$ integrin, respectively, and reduce off-target sequestration of the modified Ad5 serotype adenovirus to the liver and spleen, and the adenovirus is viable.

2. The adenovirus according to claim 1 further comprising a 24-base pair deletion d1922-947 in the E1A gene.

3. The adenovirus according to claim 2 further comprising a single adenine base addition at position 445 within the endoplasmic reticulum (ER) retention domain in E3/19K.

4. The adenovirus according to claim 1 further comprising—a single adenine base addition at position 445 within the endoplasmic reticulum (ER) retention domain in E3/19K.

5. The adenovirus according to claim 1 further comprising a transgene encoding a therapeutic molecule or agent.

6. The adenovirus according to claim 1 wherein the tumor targeting mutation comprises:

(i) an A20 peptide insertion in the viral fiber knob HI loop, (ii) an insertion of a peptide comprising a NGR motif in the HI loop of the adenoviral fiber protein, or

13. The adenovirus according to claim 6 further comprising a single adenine base addition at position 445 within the endoplasmic reticulum (ER) retention domain in E3/19K.

14. A composition comprising the adenovirus according to claim 1 and carrier, adjuvant, diluent, excipient, or vehicle.

15. A method for preparing the composition according to claim 14, comprising admixing the adenovirus with the carrier, adjuvant, diluent, excipient, or vehicle.

16. A method for treating cancer comprising administering an effective amount of the pharmaceutical composition according to claim 14 to a patient in need thereof.

17. The method according to claim 16 wherein said cancer is selected from the group comprising: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, cancer of the larynx, pleural cancer, salivary gland cancer, tongue cancer and tonsil cancer.

18. A method for treating cancer comprising administering an effective amount of the adenovirus according to claim 1 to a patient in need thereof.

19. A method (i) for preventing an Ad5 serotype adenovirus from binding with coagulation factor 10 (FX), coxsackie and adenovirus receptor (CAR) and $\alpha v\beta_3/\alpha v\beta_5$ integrin, and (ii) for reducing off-target sequestration of the Ad5 serotype adenovirus to the liver and spleen, and (iii) for having the Ad5 serotype adenovirus target tumor cells,
said method comprising:
  modifying the Ad5 serotype adenovirus, whereby the Ad5 serotype adenovirus comprises:
  a) mutation in the hexon hypervariable region 7 (HVR7 mutation);
  b) mutation in the fiber knob region AB loop (KO1 mutation); and
  c) mutation in the penton integrin binding motif Arg-Gly-Asp (RGD mutation); and
  d) a tumor-cell targeting mutation;
wherein:
  the HVR7 mutation comprises I421G, T423N, E424S, E450Q and L426Y;
  the KO1 mutation comprises S408E and P409A; and
  the RGD mutation comprises D342E;
whereby the Ad5 serotype adenovirus is prevented from binding with FX, CAR, and $\alpha v\beta_3/\alpha v\beta_5$ integrin, and exhibits reduced off-target sequestration to the liver and spleen, and
whereby:
  the adenovirus targets tumor cells; and
  the adenovirus is viable.

20. A modified Ad5 serotype adenovirus having mutations comprising mutations that prevent the modified Ad5 serotype adenovirus binding with coagulation factor 10 (FX), the coxsackie and adenovirus receptor (CAR), and $\alpha v\beta_3/\alpha v\beta_5$ integrin, and that reduce off-target sequestration of the modified Ad5 serotype adenovirus to the liver and spleen, said mutations comprising:
  a) I421G, T423N, E424S, E450Q and L426Y mutations in the hexon hypervariable region 7 (HVR7 mutation);
  b) S408E and P409A mutations in the fiber knob region AB loop (KO1 mutation); and
  c) D342E mutation in the penton integrin binding motif Arg-Gly-Asp (RGD mutation);
whereby:
  the HVR7 mutation, KO1 mutation, and RGD mutation prevent virus binding with FX, CAR, and $\alpha v\beta_3/\alpha v\beta_5$ integrin, respectively, and reduce off-target sequestration of the modified Ad5 serotype adenovirus to the liver and spleen.

21. The adenovirus according to claim 20 further comprising a 24-base pair deletion d1922-947 in the E1A gene.

22. The adenovirus according to claim 20, further comprising a single adenine base addition at position 445 within the endoplasmic reticulum (ER) retention domain in E3/19K.

23. The adenovirus of claim 20 further comprising a trans gene encoding a therapeutic molecule or agent.

24. A composition comprising the adenovirus according to claim 20 and a carrier, adjuvant, diluent, excipient, or vehicle.

25. A method for preparing the composition according to claim 24, comprising admixing the adenovirus with the carrier, adjuvant, diluent, excipient, or vehicle.

26. A method for preventing an Ad5 serotype adenovirus from binding with coagulation factor 10 (FX), coxsackie and adenovirus receptor (CAR) and $\alpha v\beta_3/\alpha v\beta_5$ integrin, and for reducing off-target sequestration of the Ad5 serotype adenovirus to the liver and spleen,
said method comprising:
  modifying the Ad5 serotype adenovirus, whereby the Ad5 serotype adenovirus comprises:
  a) mutation in the hexon hypervariable region 7 (HVR7 mutation);
  b) mutation in the fiber knob region AB loop (KO1 mutation); and
  c) mutation in the penton integrin binding motif Arg-Gly-Asp (RGD mutation); and
wherein:
  the HVR7 mutation comprises I421G, T423N, E424S, E450Q and L426Y;
  the KO1 mutation comprises S408E and P409A; and
  the RGD mutation comprises D342E;
whereby
  the Ad5 serotype adenovirus is prevented from binding with FX, CAR, and $\alpha v\beta_3/\alpha v\beta_5$ integrin, and exhibits reduced off-target sequestration to the liver and spleen.

* * * * *